United States Patent
Garcia et al.

(10) Patent No.: US 6,482,950 B1
(45) Date of Patent: Nov. 19, 2002

(54) SQUARYLIUM COMPOUNDS, AND PROCESSES AND INTERMEDIATES FOR THE SYNTHESIS OF THESE COMPOUNDS

(75) Inventors: Paulina P. Garcia, Arlington, MA (US); John W. Lee, Still River, MA (US); John L. Marshall, Somerville, MA (US); Donald A. McGowan, Bedford, MA (US); Anthony J. Puttick, Arlington, MA (US); Thomas K. Spencer, Lexena, KS (US); Stephen G. Stroud, Medford, MA (US); Stephen J. Telfer, Arlington, MA (US); Michael J. Zuraw, Arlington, MA (US)

(73) Assignee: Polaroid Corporation, Cambridge, MA (US)

( * ) Notice: Subject to any disclaimer, the term of this patent is extended or adjusted under 35 U.S.C. 154(b) by 0 days.

(21) Appl. No.: 08/479,077

(22) Filed: Jun. 6, 1995

Related U.S. Application Data

(60) Division of application No. 08/052,212, filed on Apr. 23, 1993, now Pat. No. 5,919,950, which is a continuation-in-part of application No. 07/696,222, filed on Jan. 6, 1991, now Pat. No. 5,231,190.

(51) Int. Cl.[7] ............... C07D 471/00; C07D 335/00; C07D 409/00; C07D 311/04
(52) U.S. Cl. ............... 546/66; 549/13; 549/23; 549/407; 549/427; 562/899
(58) Field of Search ............... 546/66; 549/13, 549/23, 407, 427; 562/899

(56) References Cited

U.S. PATENT DOCUMENTS

| | | | |
|---|---|---|---|
| 3,617,270 A | 11/1971 | Kampfer | 430/62 |
| 4,175,956 A | 11/1979 | Haley et al. | 430/37 |
| 4,343,948 A | 8/1982 | Kawamura et al. | 549/13 |
| 4,353,971 A | 10/1982 | Chang et al. | 430/58 |
| 4,387,155 A | 6/1983 | Hill et al. | 430/215 |
| 4,507,480 A | 3/1985 | Horgan et al. | 546/94 |
| 4,508,811 A | 4/1985 | Gravesteijn et al. | 430/270 |
| 4,524,219 A | 6/1985 | Law | 564/307 |
| 4,585,884 A | 4/1986 | Lin et al. | 556/413 |
| 4,585,895 A | 4/1986 | Law | 564/307 |
| 4,602,263 A | 7/1986 | Borrer et al. | 346/201 |
| 4,606,986 A | 8/1986 | Yanus et al. | 430/59 |
| 4,624,904 A | 11/1986 | Kazmaier et al. | 430/59 |

(List continued on next page.)

FOREIGN PATENT DOCUMENTS

| | | |
|---|---|---|
| JP | 220143/83 | 12/1983 |
| JP | 167681/86 | 7/1986 |
| WO | WO 88/04237 | 6/1988 |

OTHER PUBLICATIONS

Anderson and Stang, J. Org. Chem. 41, 3034 (1976).
Chemical Abstracts 107, 43057u (1987), and CAS on–line print–out.

(List continued on next page.)

Primary Examiner—Deborah C. Lambkin

(57) ABSTRACT

Squarylium compounds of the formula:

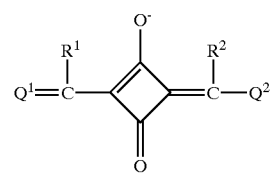

(I)

wherein $Q^1$ and $Q^2$ are each independently a pyrylium, thiopyrylium, selenopyrylium, benzpyrylium, benzthiopyrylium or benzselenopyrylium nucleus, and $R^1$ and $R^2$ are each independently an aliphatic or cycloaliphatic group, can be prepared by reacting a squaric acid derivative of the formula:

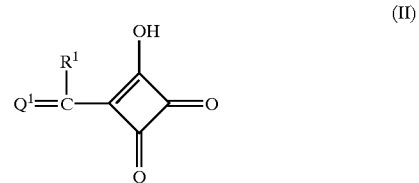

(II)

with a compound of the formula $Q^2CH_2R^2$ in the presence of a base. The derivatives of Formula II may be prepared by condensing a 2,3,4,4-tetrahalocyclobut-2-en-1-one with a compound of the formula $Q^1CH_2R^1$ in the presence of a base to produce a compound of the formula:

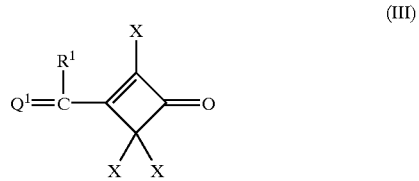

(III)

wherein $Q^1$ and $R^1$ are as defined above, and X represents chlorine or bromine, and hydrolyzing the compound of Formula III. Alternatively, the derivatives of Formula II may be prepared by reacting a diester, monoacid chloride monoester or diacid chloride of squaric acid with a compound of the formula $Q^1CH_2R^1$ in the presence of a base, followed by hydrolysis of the resultant monoacid chloride or monoester derivative of the compound of Formula II to the parent compound.

10 Claims, 7 Drawing Sheets

U.S. PATENT DOCUMENTS

| | | | | |
|---|---|---|---|---|
| 4,663,518 | A | | 5/1987 | Borrer et al. ............... 235/487 |
| 4,751,327 | A | | 6/1988 | Kazmaier et al. ........... 564/307 |
| 4,826,976 | A | | 5/1989 | Borrer et al. .............. 544/58.4 |
| 4,830,786 | A | | 5/1989 | Pease et al. ................. 260/396 |
| 4,886,722 | A | | 12/1989 | Law et al. ..................... 430/59 |
| 4,922,018 | A | | 5/1990 | Law et al. .................. 564/307 |
| 4,927,970 | A | | 5/1990 | Douglas et al. ............. 564/462 |
| 5,026,923 | A | | 6/1991 | Kemp ........................ 568/618 |
| 5,028,660 | A | | 7/1991 | Kubashi et al. ............. 528/148 |
| 5,030,684 | A | | 7/1991 | Rouch-Puntigameld ..... 524/513 |
| 5,030,759 | A | | 7/1991 | Bayer et al. ................ 564/901 |
| 5,079,127 | A | * | 1/1992 | Katagirl et al. ............. 430/269 |
| 5,084,592 | A | | 1/1992 | Schrott et al. .............. 558/162 |

OTHER PUBLICATIONS

Chemical Abstracts 99, 61698z (1983), and CAS on–line print–out.

Cohen S. and Cohen, S. G., J. Am. Chem. Soc., 88, 1533 (1966).

DeSelms, R.C., Fox, C.J., and Riordan, R.C., Tetrahedron Letters, 1970, 781.

Detty, M.R., and Murray, B.J., J. Am. Chem. Soc., 105, 883–890 (1983).

Hackh's Chemical Dictionary, 4th Edn., McGraw–Hill, New York (1964), p. 26.

Hori et al., Angew. Chem. Int. Edn. 29(4), 424–425 (1990).

Kazmaier et al., "The Photogenerating Properties of Unsymmetrical Squaraines and Squaraine Composites", J. Imag. Sci., 32, 1–4 (1988).

Kuramoto et al., Dyes and Pigments, 11, 21–35 (1989).

Liebeskind et al., J. Org. Chem. 53, 2482 (1988).

Maahs, et al., "Syntheses and Derivatives of Squaric Acid", Angew. Chem. Int. Ed., 5, 888–893 (1966).

March, J., Advanced Organic Chemistry: Reactions, Mechanisms and Structure, (3d Edn.), Wiley, New York (1985), pp. 326–327.

Metler, T. et al., Tetrahedron, 24, 4285 (1968).

Mueller et al., Liebig's Ann. Chem, (1973), 1583.

Nakagawa, K., et al., J. Org. Chem., 27, 1597 (1962).

Palmer, M., The Structure and Reactions of Heterocyclic Compounds, Arnold, London (1967), pp. 252–255.

Schmidt, A. H., Synthesis, 1980, 961.

Triebs, A., and Jacob, K., Liebigs Ann. Chem., 712, 123 (1968).

Von Strandtmann et al., J. Het. Chem., 9, 171 (1972).

* cited by examiner

SQUARYLIUM COMPOUNDS, AND PROCESSES AND INTERMEDIATES FOR THE SYNTHESIS OF THESE COMPOUNDS

REFERENCE TO PARENT APPLICATION

This application is a divisional of our application Ser. No. 08/052,212, filed Apr. 23, 1993 U.S. Pat. No. 5,919,950 which a continuation-in-part of our application Ser. No. 07/696,222, filed Jan. 6, 1991, now Pat. No. 5,231,190.

REFERENCES TO RELATED APPLICATIONS

U.S. patent application Ser. No. 07/795,034, filed Nov. 20, 1991 (now U.S. Pat. No. 5,227,498), U.S. patent application Ser. No. 07/979,250, filed Nov. 20, 1992 and International Application PCT/US92/09992 (Publication No. WO 93/09956, all describe amino-substituted squarylium infra-red dyes, including (in the last two applications) dyes containing 6-alkoxybenzpyrylium nuclei.

U.S. patent application Ser. No. 07/795,038, filed Nov. 20, 1991, describes and claims bis(benzpyrylium) squarylium dyes, including certain asymmetric dyes produced by processes of the present invention.

U.S. patent application Ser. No. 07/965,161, filed Oct 23, 1992 now U.S. Pat. No. 5,286,612, describes a process for generation of acid, which process comprises:

providing a medium containing a mixture of a superacid precursor and a dye capable of absorbing actinic radiation of a first wavelength which does not, in the absence of the dye, cause decomposition of the superacid precursor to form the corresponding superacid, the superacid precursor being capable of being decomposed by actinic radiation of a second wavelength shorter than the first wavelength;

irradiating the medium with actinic radiation of the first wavelength, thereby causing absorption of the actinic radiation, and decomposition of part of the superacid precursor, without formation of free superacid but with formation of a protonated product derived from the dye; and thereafter irradiating the medium with actinic radiation of the second wavelength, thereby causing decomposition of part of the remaining superacid precursor, with formation of free superacid.

At least some of the dyes produced by the process of the present invention may be used in the process of this copending application.

The disclosures of the aforementioned U.S. applications and patents are herein incorporated by reference.

BACKGROUND OF THE INVENTION

This invention relates to squarylium compounds, and processes and intermediates for the synthesis of these compounds. More specifically, this invention relates to processes and intermediates useful for the synthesis of squarate dyes (and to such dyes themselves) in which two heterocyclic nuclei are linked to the 1- and 3-positions of a squarate ring via a single $sp^2$ hybridized carbon atom (hereinafter called the "meso" carbon atom); these dyes will hereinafter be called "pentamethine squarate dyes". The processes of the present invention are especially useful for the synthesis of asymmetric pentamethine squarate dyes, i.e., those in which the two heterocyclic nuclei are dissimilar. The present invention is also useful for the synthesis of related dyes in which one meso carbon atom and its associated heterocyclic nucleus are replaced by an aromatic nucleus directly bonded to the squarylium ring.

It is known that compounds in which two heterocyclic nuclei are linked by a pentamethine chain, the three central carbon atoms of which form part of a squarate ring, are useful as dyes, especially near infra-red dyes. (The term "near infra-red" is used herein to mean electromagnetic radiation having a wavelength of about 700 to about 1200 nm.) For example, Japanese Patent Application No. 103,604/82 (Publication No. 220,143/83, published Dec. 21, 1983), discloses a broad class of bis-heterocyclic pentamethine dyes in which the central three carbon atoms of the pentamethine chain form part of a squarylium or croconylium ring. The heterocyclic nuclei can be pyrylium, thiopyrylium, selenopyrylium, benzpyrylium, benzthiopyrylium, benzselenopyrylium, naphthopyrylium, naphthothiopyrylium or naphthoselenopyrylium nuclei, which can be substituted with alkyl, alkoxy, aryl or styryl groups.

Japanese Patent Application No. 60-8730 (Publication No. 167,681/86, published Jul. 29, 1986), discloses bis(4-benz[b]thiopyrylium) pentamethine dyes in which the central three carbon atoms of the pentamethine chain form part of a squarylium ring. The dyes are intended for use as infra-red absorbers.

U.S. Pat. No. 4,508,811, issued Apr. 2, 1985, describes an optical recording element in which the recording layer comprises a bis(2,6-dialkyl)-pyrylium or -thiopyrylium squarylium salt.

Application Ser. No. 07/616,639, filed Nov. 21, 1990 (now abandoned) by Stephen J. Telfer et al. and assigned to the same assignee as the present application, and the aforementioned U.S. patent application Ser. No. 07/795,038, describe 4-[[3-[(benz[b]-4H-pyran-4-ylidene)methyl]-2-hydroxy-4-oxo-2-cyclobuten-1-ylidene]methyl]benz[b] pyrylium hydroxide inner salt dyes, in which at least one benzpyrylium nucleus carries at its 2-position a substituent in which a non-aromatic carbon atom is bonded directly to the benzpyrylium nucleus, subject to the proviso that if this 2-substituent contains an aromatic nucleus, this aromatic nucleus is not conjugated with the benzpyrylium nucleus. These dyes have high absorptions in the near infra-red, and improved solubility in semi-polar solvents and plastics.

Most of these aforementioned pentamethine squarate dyes are symmetrical, that is to say the two heterocyclic nuclei are the same. Such symmetrical dyes are typically prepared by condensing two moles of the appropriate alkyl-substituted heterocyclic compound (usually, a salt) with squaric acid in the presence of a-base.

In certain applications of pentamethine squarate dyes, it may be advantageous to use a dye which is asymmetric, i.e., which contains two different heterocyclic groupings. For example, some symmetrical near infra-red pentamethine squarate dyes have significant absorption in the visible region, and this visible absorption restricts the utility of the dyes in certain applications, for example thermal imaging media. In particular, if the symmetrical dye absorbs strongly in one part of the visible spectrum but not in another, it will tend to introduce color distortion into any image created using the symmetrical dye. Although asymmetrical analogues of these infra-red pentamethine squarate dyes may have some visible absorption, this visible absorption tends to take the form of several separate small peaks, and is thus more spread out over a wide range of wavelengths than in the symmetrical dyes. Such absorption over a range of wavelengths tends to produce lower peak absorption and less color distortion (because the dye tends to produce a grey tint) than that produced by the symmetrical dyes, and thus the asymmetric dyes may advantageously be used in applications where the visible absorption of the symmetric dyes causes problems.

Moreover, there are a number of applications where infra-red dyes are needed which absorb at specific wavelengths. For example U.S. Pat. Nos. 4,602,263 and 4,826,976 both describe thermal imaging systems for optical recording and particularly for forming color images. These patents describe a preferred form of thermal imaging medium for forming multicolor images; in this preferred imaging medium, three separate color-forming layers, capable of forming yellow, cyan and magenta dyes respectively, are superposed on top of one another. Each of the three color-forming layers has an associated infra-red absorber, these absorbers absorbing at differing wavelengths, for example 760, 820 and 880 nm. This medium is imagewise exposed simultaneously to three lasers having wavelengths of 760, 820 and 880 nm. The resultant imagewise heating of the color-forming layers causes the leuco dyes to undergo color changes in the exposed areas, thus producing a multicolored image, which needs no development. If the choice of infra-red dyes is restricted to symmetrical compounds, it may be difficult to find a dye which absorbs at the precise wavelength required, and which meets the other requirements, such as storage stability and miscibility in polymers, for use in such media. Asymmetric dyes, which allow the two groups linked to the squarylium nucleus to be varied independently, provide an extra degree of freedom, which renders it easier to find a dye which absorbs at the desired wavelength and meets the other requirements for use in such media.

However, despite the potential advantages of asymmetric pentamethine squarate dyes, little research has been conducted on such dyes because of the difficulties involved in their synthesis. Although it is possible to modify the conventional alkyl-substituted heterocyclic compound/squaric acid condensation reaction to produce asymmetric pentamethine dyes by including two different heterocyclic compounds in the reaction mixture, such a modified process inevitably produces three different products (two symmetrical dyes and the desired asymmetric dye), thus wasting at least half the starting materials (and possibly more if one heterocyclic compound is significantly more reactive than the other). Given that the costs of some symmetric pentamethine squarate dyes are high, such materials should be used judiciously and their loss minimized where possible.

Furthermore, separation of the tertiary product mixture produced is difficult, especially since, in many cases of practical importance, the two heterocyclic compounds used are chemically similar. For example, if one attempts to produce the dye of Formula A shown in FIG. 1 in which $R^1$ and $R^2$ are each a hydrogen atom (this dye contains one pyrylium nucleus and one selenopyrylium nucleus) simply by condensing a mixture of the two corresponding salts with squaric acid, it is extremely difficult to separate the desired asymmetric salt from the two, even on a laboratory scale, and conducting this separation on a commercial scale would be a practical impossibility. In some applications of infra-red dyes, the presence of even minor amounts of symmetric by-products in the desired asymmetric dye may cause significant problems. For example, as already noted, in the thermal imaging media described in the aforementioned U.S. Pat. Nos. 4,602,263 and 4,826,976, three separate imaging layers are present having infra-red absorbers with absorptions at 760, 820 and 880 nm. Conveniently, two of these three absorbers are Dye A shown in FIG. 1, in which $R^1$ and $R^2$ are each a hydrogen atom, and the corresponding bis-selenopyrylium dye. However, if Dye A is contaminated with even a small proportion of the corresponding bis-selenopyrylium dye, serious problems may result in such a medium, in that the bis-selenopyrylium impurity in the layer containing Dye A will absorb the "wrong" radiation, which may lead to unwanted exposure of parts of the layer containing Dye A and a reduction in sensitivity of the medium because the bis-selenopyrylium impurity will absorb a large part of the radiation intended to cause color change in a different color-forming layer.

There is thus a need for a process for the preparation of pentamethine squarate dyes, which does not require the separation of mixtures of asymmetric and symmetric products, and which can avoid waste of starting materials.

Processes for the preparation of asymmetric compounds, in which two different aromatic nuclei are directly bonded to a squarate ring, are known. Kazmaier et al., "The Photogenerating Properties of Unsymmetrical Squaraines and Squaraine Composites", J. Imag. Sci., 32, 1–4 (1988) states that unsymmetrical squaraines can be produced by a two-step route in which the two pendent aromatic groups are attached in separate reactions, and further states that "Unsymmetrical squaraines were synthesized in a multi-step procedure featuring the preparation of 4-(4-dimethylaminophenyl)-3-hydroxycyclobutenedione". However, no further details of this procedure are given.

U.S. Pat. No. 4,751,327 and U.S. Pat. No. 4,624,904 describe unsymmetrical squaraines for use in photoconductive imaging members. Columns 8–10 of each patent describe two synthetic methods for the preparation of these squaraines, these methods involving condensation of a diacid chloride or diester of squaric acid with one mole of a first amine, to form the appropriate 4-aminophenyl squarate derivative, hydrolysis of this derivative to introduce a 2-hydroxyl group on the squarate ring, and a second condensation to introduce at the 3-position of the squarate ring a second and different 4-aminophenyl group.

U.S. Pat. No. 4,922,018 and U.S. Pat. No. 4,886,722 describe unsymmetrical squaraines and their use in photoconductive imaging members. These squaraines are prepared by condensing, for example, a 1-alkoxyaryl-2-hydroxycyclobutene-3,4-dione derivative with an N,N-dialkylaniline derivative in the presence of an aliphatic alcohol and optionally a drying reagent. The squarate derivative is formed by a 2+2 cycloaddition process involving a tetraalkoxyolefin and an alkoxyarylketene generated in situ by the reaction of an alkoxyarylacetyl chloride and a base. The conditions of this cycloaddition reaction limit the substituents which can be present on the alkoxyarylacetyl chloride. Furthermore, the syntheses of the alkoxyarylacetyl chlorides required may be difficult.

The present invention provides processes, which can be used to prepare asymmetric pentamethine squarate and related dyes, and intermediates produced by such processes.

SUMMARY OF THE INVENTION

This invention provides a process for the preparation of a squarylium compound of the formula:

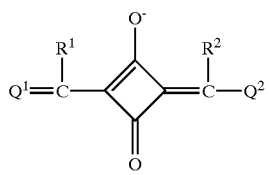

(I)

wherein $Q^1$ and $Q^2$ are each independently an aromatic heterocyclic nucleus such that in the compounds of formulae $Q^1CH_2R^1$ and $Q^2CH_2R^2$ the methylene hydrogens are active hydrogens, and $R^1$ and $R^2$ are each independently a hydrogen atom or an aliphatic or cycloaliphatic group. This process comprises reacting a squaric acid derivative of the formula:

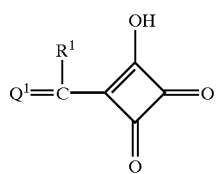

(II)

wherein $Q^1$ and $R^1$ are as defined above, with a compound of the formula $Q^2CH_2R^2$. This reaction, hereinafter called the "salt dye-forming" reaction of the invention, is desirably conducted in the presence of either a base or a Lewis acid (for example, titanium tetrachloride).

This invention also provides a squarylium compound of Formula I above wherein $Q^1$ and $Q^2$ are each independently a pyrylium, thiopyrylium, selenopyrylium, benzpyrylium, benzthiopyrylium or benzselenopyrylium nucleus, and $R^1$ and $R^2$ are each independently a hydrogen atom or an aliphatic or cycloaliphatic group, the $Q^1CR^1$ grouping being different from the $Q^2CR^2$ grouping.

This invention also provides a first process for the preparation of a squaric acid derivative of Formula II as defined above, which process comprises hydrolyzing a trihalosquaric acid derivative of the formula:

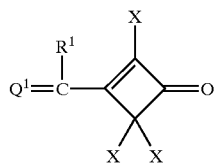

(III)

wherein $Q^1$ and $R^1$ are as defined above, and X represents chlorine or bromine. This process will hereinafter be called the "trihalosquaric hydrolysis" reaction of the invention.

This invention also provides a second process for the preparation of a squaric acid derivative of Formula II as defined above, which process comprises reacting a diester, monoacid chloride monoester or diacid chloride of squaric acid with a compound of the formula $Q^1CH_2R^1$ (wherein $Q^1$ is a heterocyclic nucleus such that in the compound of formula $Q^1CH_2R^1$ the methylene hydrogens are active hydrogens, subject to the proviso that in $Q^1$ a carbon atom is bonded to the carbon atom carrying the group $R^1$, and this carbon atom is not bonded directly to a nitrogen atom, and $R^1$ is as defined above), followed by hydrolysis of the resultant monoacid chloride or monoester intermediate. This reaction will hereinafter be called the "salt condensation" reaction of the invention.

This invention also provides a third process for the preparation of a squaric acid derivative of the formula:

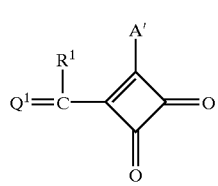

(IV)

wherein $Q^1$ is a 4-pyrylium, 4-thiopyrylium, 4-selenopyrylium, 4-benzpyrylium, 4-benzthiopyrylium or 4-benzselenopyrylium nucleus, $R^1$ is a hydrogen atom or an aliphatic or cycloaliphatic group, and A' is an esterified hydroxyl group; the compounds of Formula IV are of course esters of the compounds of Formula II.

This process comprises reacting a chromone of the formula $Q^1=O$ with a squaric acid derivative of the formula:

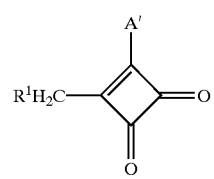

(V)

This process will hereinafter be called the "chromone condensation" reaction of the invention. The resultant ester of Formula IV may of course be hydrolyzed to the corresponding hydroxyl compound of Formula II by conventional methods.

This invention also provides a process for the preparation of a trihalosquaric acid derivative of Formula (III) as defined above, which process comprises condensing a 2,3,4,4-tetrahalocyclobut-2-en-1-one with a compound of the formula $Q^1CH_2R^1$ in the presence of a base. This reaction will hereinafter be called the "trihalosquaric formation reaction".

This invention also provides a squaric acid derivative of Formula III above, in which $Q^1$ is an aromatic heterocyclic nucleus such that in the compounds of formulae $Q^1CH_2R^1$ the methylene hydrogens are active hydrogens and $R^1$ is a hydrogen atom or an aliphatic or cycloaliphatic group; and each X is a chlorine or bromine atom.

This invention also provides a squaric acid derivative of the formula:

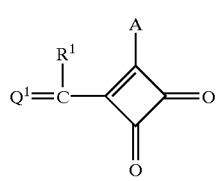

(VI)

wherein $Q^1$ is a heterocyclic nucleus such that in the compounds of formulae $Q^1CH_2R^1$ the methylene hydrogens are active hydrogens and $R^1$ is a hydrogen atom or an aliphatic or cycloaliphatic group; and A is a chlorine or bromine atom, a hydroxyl group or an esterified hydroxyl group.

Finally, this invention provides a process for the preparation of a squarylium compound of the formula:

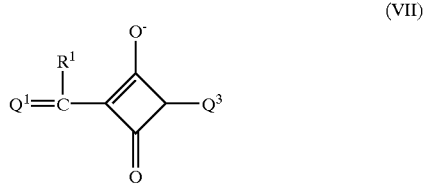

(VII)

wherein $Q^1$ and $R^1$ are as defined above, and $Q^3$ is an aromatic nucleus bearing an electron-donating group. This process comprises reacting a squaric acid derivative of Formula II as defined above, with a compound of the formula $Q^3H$. This reaction will hereinafter be called the "aromatic dye-forming" reaction of the invention.

It will be noted that the symbol $Q^1$ has been used for both a divalent grouping in Formula I and a monovalent grouping in the formula $Q^1CH_2R^1$. This apparent anomaly arises because the bond orders in the compounds of Formula I (and indeed in the compounds of Formulae II-VII also) are not integral. For example, the dye A shown in FIG. 1 is actually a resonance hybrid of the form shown and:

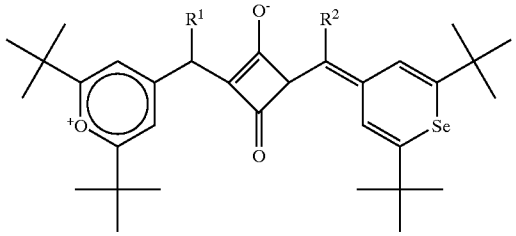

(with contributions from other resonance forms). Thus, whether $Q^1$ is drawn as divalent or monovalent depends solely upon which of the contributing resonance forms is drawn, and similarly for $Q^2$. On the other hand, the compounds of formula $Q^1CH_2R^1$, such as the salt B shown in FIG. 1, are not resonance hybrids to any significant extent, and thus in this formula $Q^1$ is correctly shown as monovalent. The $Q^1/Q^2$ nomenclature employed will thus be clear to skilled chemists.

The dyes produced by the processes of the present invention may be cationic, anionic or non-ionic. When neither of the nuclei $Q^1$ and $Q^2$ ($Q^1$ and $Q^3$ in dyes of Formula VII) carries any charged substituents, the $Q^1Q^2$-squarate moiety (or the $Q^1Q^3$-squarate moiety; either moiety is hereinafter called simply the "dye moiety") is uncharged, and hence the dye is non-ionic. However, if either of the nuclei $Q^1$ and $Q^2$ (or $Q^1$ and $Q^3$) carries a negatively or positively charged group (for example a —COO— or trialkylammonium substituent), the dye will be anionic or cationic respectively, and will contain a counterion.

When such a counterion is present, it may be any counterion which is not incompatible with the dye moiety and which thus provides a stable salt. The choice of counterion may be important in ensuring the solubility of the dye in various media, and reducing or preventing aggregation of the dye; minimizing aggregation of the dye is highly desirable since such aggregation can significantly reduce the apparent extinction coefficient of the dye in polymeric media.

Similarly, if the nucleus $Q^1$ or $Q^2$ does not carry any charged substituents (such nuclei being generally preferred in the present processes), the "compounds" $Q^1CH_2R^1$ and $Q^2CCH_2R^2$ used in the present processes are cations. The counterion present may be any counterion which provides a stable salt and does not interfere with the relevant reactions. Typically, large fluorinated anions, such as trifluoromethane sulfonate and tetrafluoroborate have been found to give good results in the present processes. The nuclei $Q^1$ and $Q^2$ may, however, bear charged substituents and thus in some cases $Q^1CH_2R^1$ and $Q^2CH_2R^2$ may be neutral compounds which do not require the presence of a counterion.

It may often be found convenient, for synthetic reasons, to prepare a desired moiety with one counterion and thereafter to effect a counterion exchange to form a different salt of the same moiety. Methods for such counterion ion exchange are well known to those skilled in the art.

DETAILED DESCRIPTION OF THE INVENTION

Figure 1:
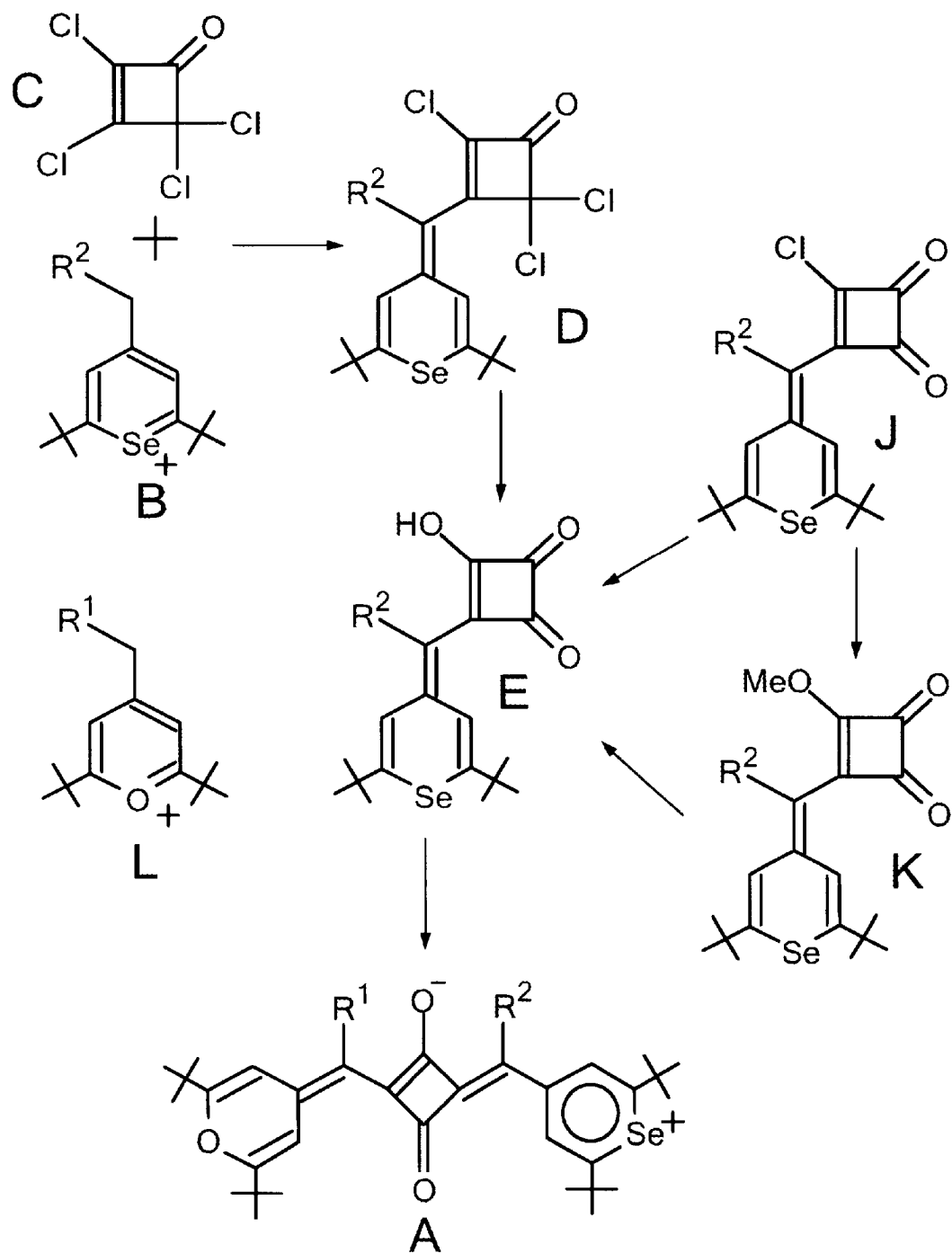
FIGS. 1 and 2 of the accompanying drawings show a synthetic scheme, which may be used to produce an asymmetric pyryliumlselenopyrylium squarate pentamethine dye of the present invention, including some of the reactions described in the Examples below.
Figure 2:
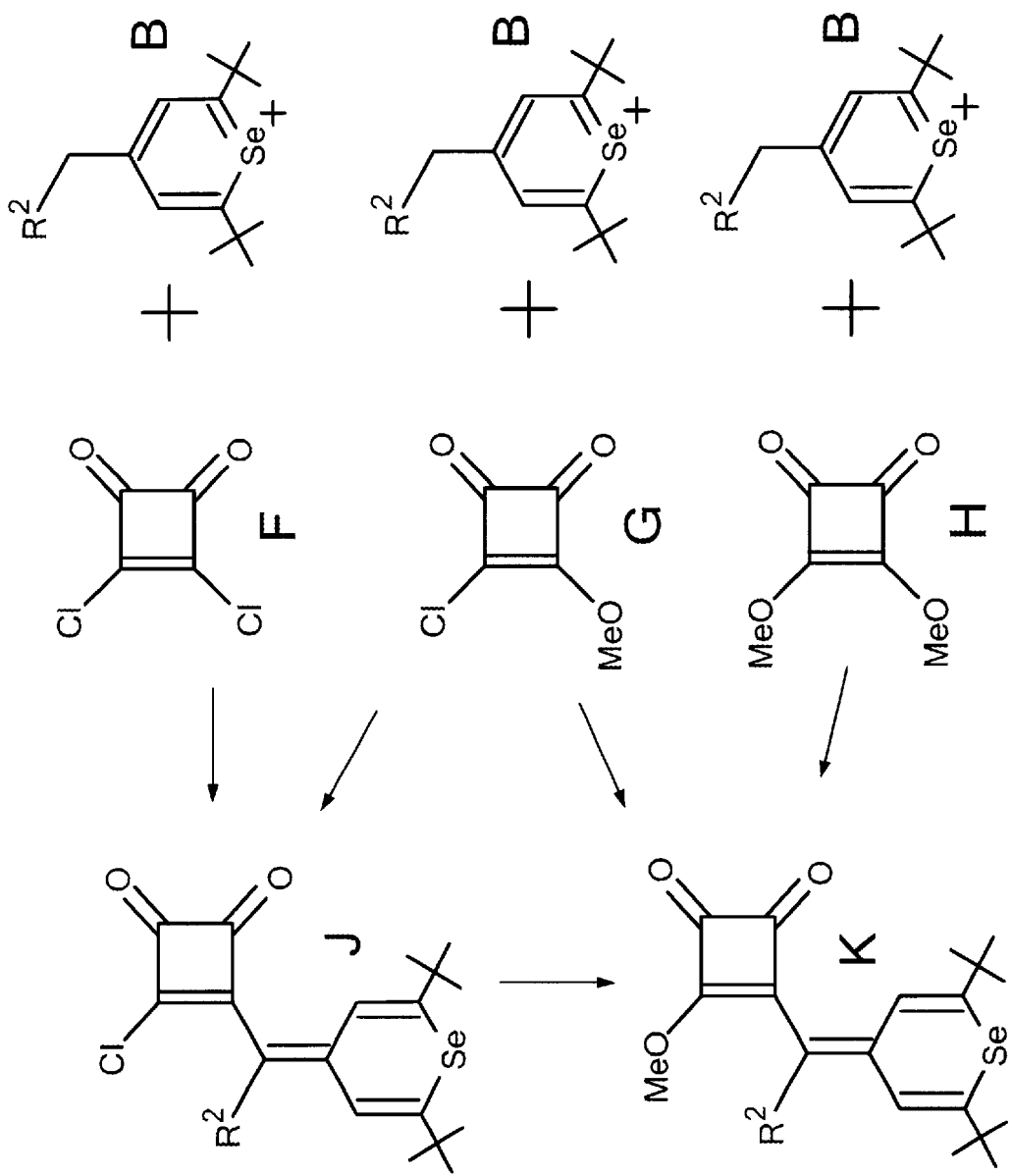
Figure 3:
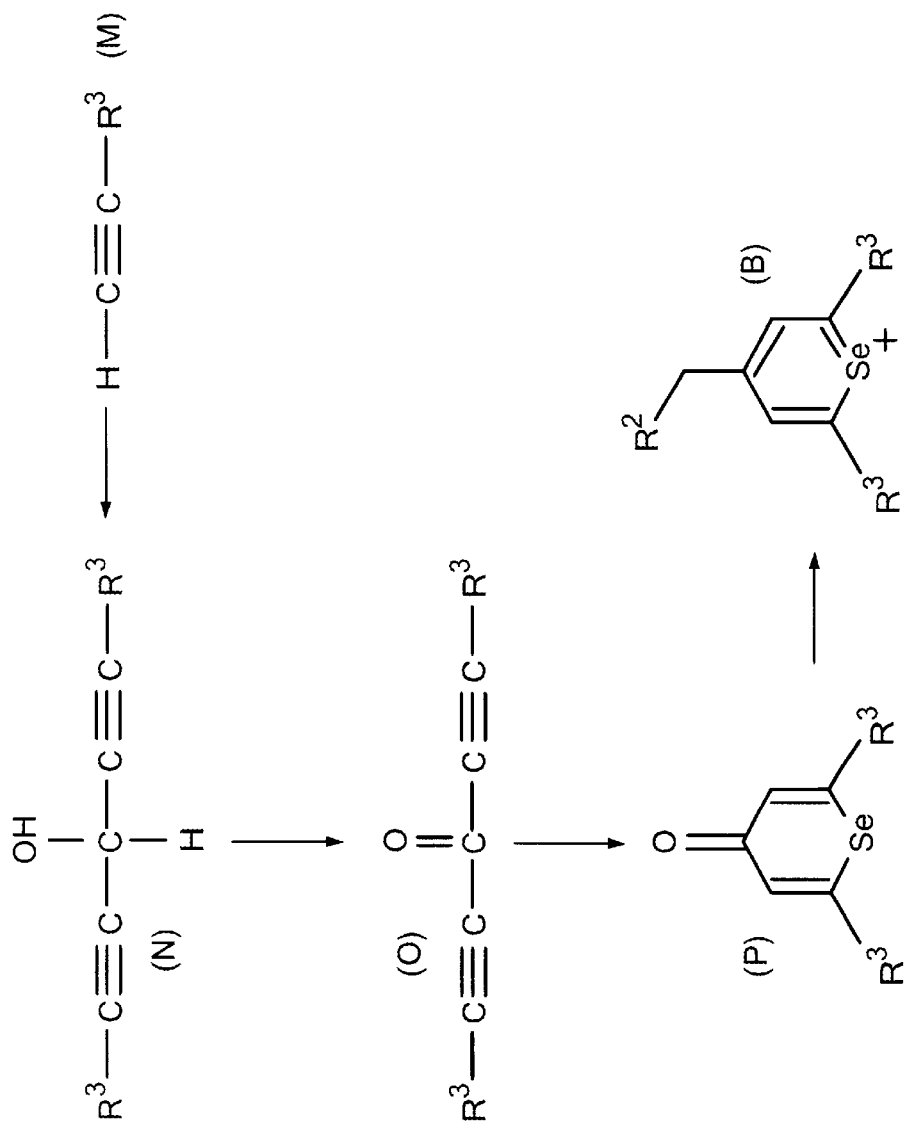
FIG. 3 shows a synthetic scheme used to produce the selenopyrylium salt of Formula B shown in FIGS. 1 and 2.
Figure 4:
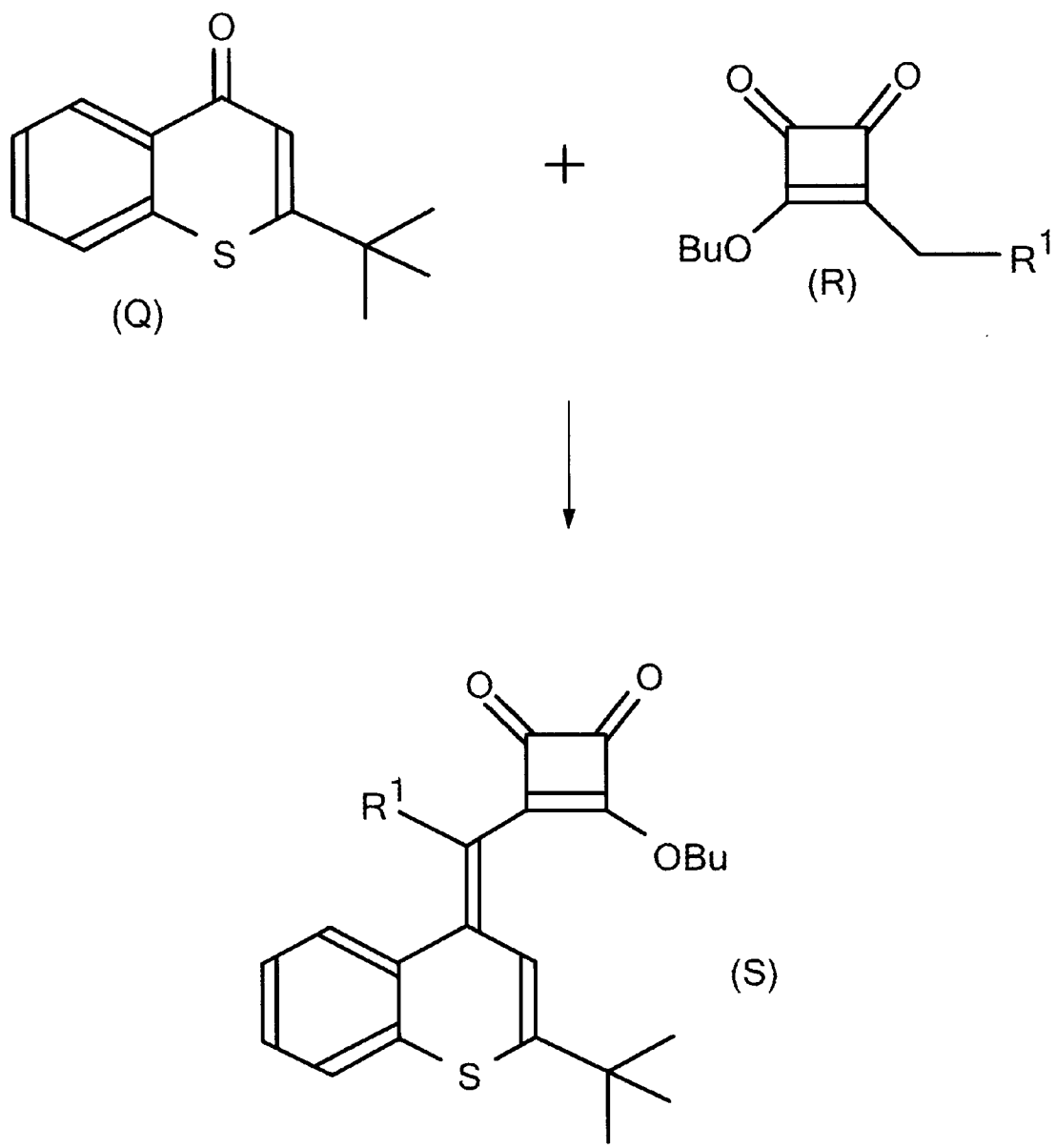
FIG. 4 shows an Example of the chromone condensation reaction of the present invention.
Figure 5:
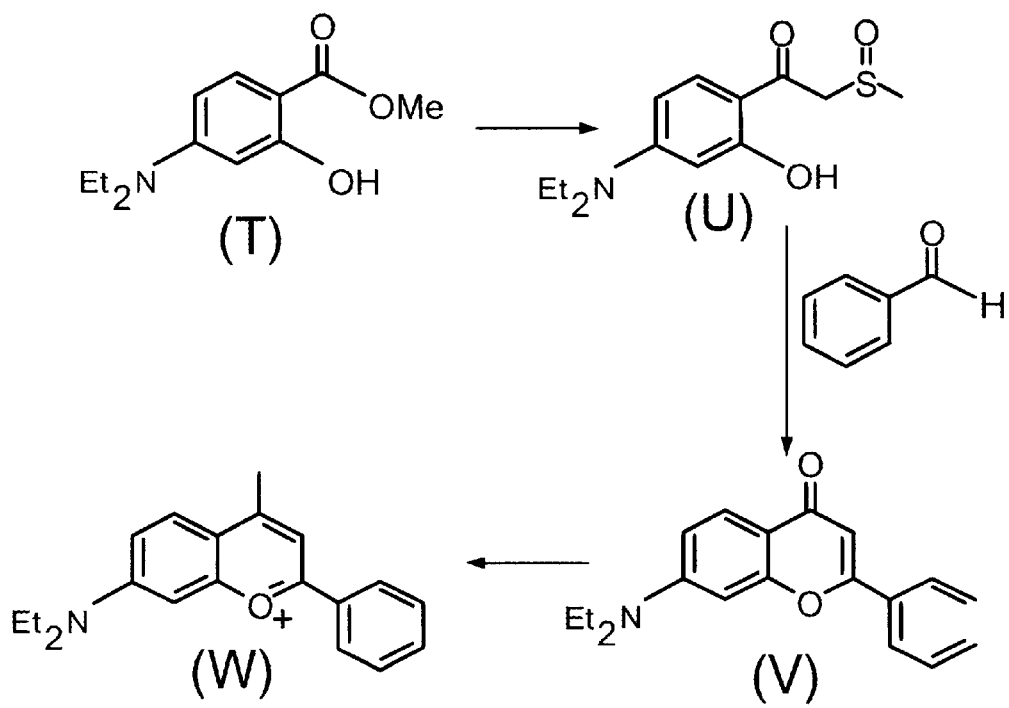
FIG. 5 shows a second synthetic scheme used to produce salts analogous to the salt of Formula B shown in FIGS. 1 and 2.
Figure 8:
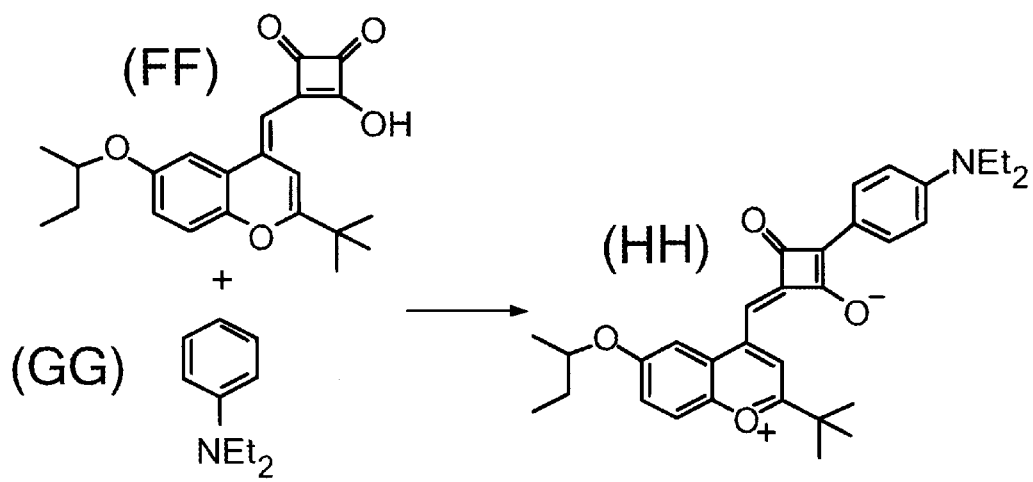
FIG. 8 shows an Example of the aromatic dye-forming reaction of the present invention.
Figure 6:
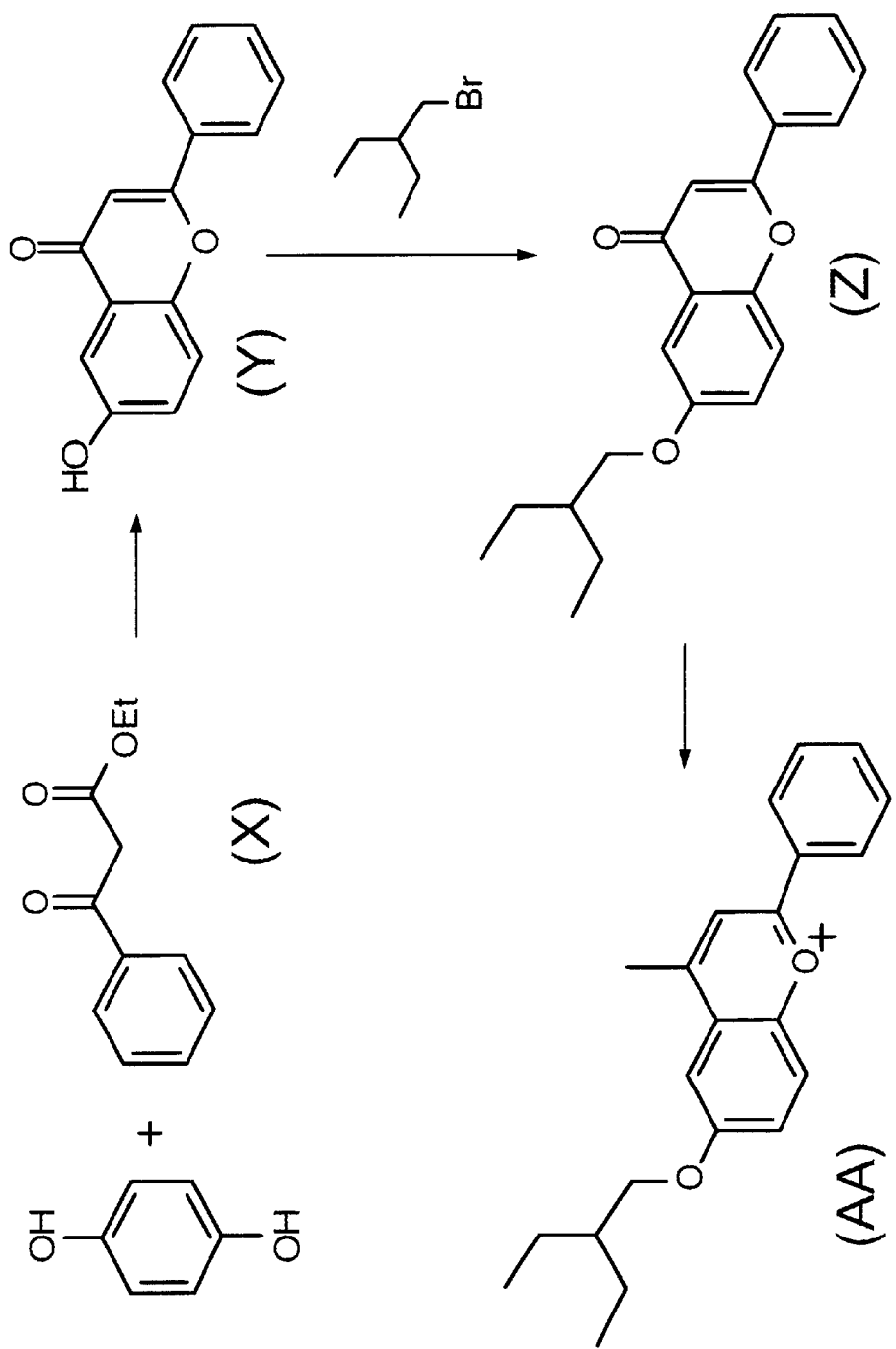
FIG. 6 shows a third synthetic scheme used to produce salts analogous to the salt of Formula B shown in FIGS. 1 and 2.
Figure 7:
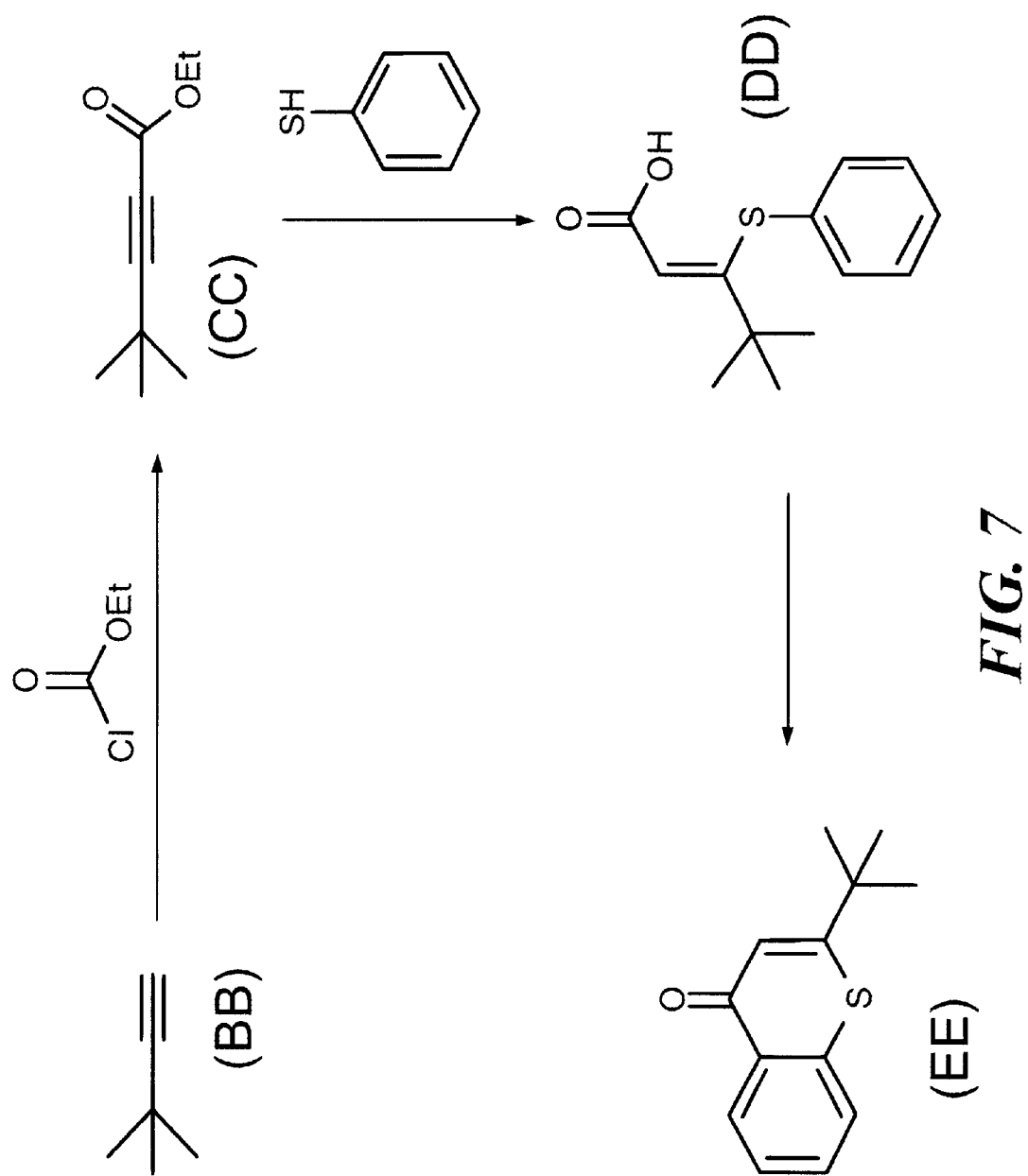
FIG. 7 shows a synthetic scheme used to produce the chromone shown in FIG. 4.

The interrelationships among the various reactions and intermediates of the present invention may best be seen from the accompanying drawings. FIGS. 1 and 2 show reactions which can be used for the synthesis of a dye A, which is the compound of Formula I in which $R^1$ and $R^2$ are each a hydrogen atom, $Q^1$ is (in the resonance hybrid drawn) a 2,6-bis(1,1-dimethylethyl)pyrylidene group, and $Q^2$ is a 2,6-bis(1,1-dimethylethyl)selenopyrylium group. FIG. 3 shows reactions which can be used to produce the selenopyrylium salt B used in the synthesis shown in FIGS. 1 and 2, while FIG. 4 shows the chromone condensation reaction of the invention being used to prepare a compound S, which is analogous to the ester intermediate K shown in FIGS. 1 and 2. FIGS. 5 and 6 show reactions which can be used, in place of those shown in FIG. 3, to prepare the salt B and analogous compounds, while FIG. 7 shows reactions which can be used to prepare the chromone used in the reaction of FIG. 4. Finally, FIG. 8 shows an example of the aromatic dye-forming reaction of the invention.

As shown in FIG. 1, one form of the synthesis begins with a trihalosquaric formation reaction, the condensation of a 2,6-bis(1,1-dimethylethyl)-4-($R^2$-methyl)pyrylium salt B (in which $R^2$ is as defined above) with 2,3,4,4-tetrachlorocyclobut-1-en-2-one C to give the trihalosquaric acid derivative D, a compound of Formula III in which each group X is a chlorine atom. The synthesis of the selenopyrylium salt B will be described below with reference to FIGS. 3, 5 and 6; alternatively, this salt may be prepared by the methods described in Murata et al., Angew. Chem. Int. Edn. 29(4), 424–425 (1990). Methods for the synthesis of the corresponding pyrylium and thiopyrylium salts are described in the literature. The tetrachloro compound C and its synthesis are described in Maahs et al., "Syntheses and Derivatives of Squaric Acid", Angew. Chem. Int. Ed., 5, 888–893 (1966).

This trihalosquaric formation reaction is conducted in the presence of a base, preferably triethylamine. (When the less reactive pyrylium salt is substituted for the selenopyrylium salt B, the reaction is conveniently effected by contacting a solution of the two reactants with a strongly basic resin, for example Baker ANGA-542 (sold by J. T. Baker, 222 Red School Lane, Phillipsburg, N.J. 08865). The solvent used is conveniently an ether, for example tetrahydrofuran. Use of stoichiometric amounts of the two starting materials gives satisfactory results. As noted above, the anion of the salt B can be any anion which provides a stable salt and does not interfere with the desired reaction; conveniently the tetrafluoroborate salt is used.

As will be apparent from FIG. 1, use of the 4-methylselenopyrylium salt B ($R^2$ is a hydrogen atom) will produce a dye in which $R^2$ is hydrogen. If the 4-methyl group of the salt B is replaced with the group of the formula —$CH_2R^2$, the corresponding dyes can be produced in which $R^2$ is an aliphatic or cycloaliphatic group; thus, for example, the use of a 4-ethyl salt gives a final dye in which $R^2$ is methyl. Similar variations in the group $R^1$ are produced by varying the 4-substituent in the pyrylium salt of Formula L (described below). It will be apparent to those skilled in the art that the tetrabromo homologue may be used in place of the tetrachloro compound C.

In the next step of the synthesis, the trihalosquaric hydrolysis reaction, the trihalosquaric acid derivative D is hydrolyzed to the corresponding non-halogenated derivative E. Desirably, this hydrolysis is effected by heating the derivative D with triflic acid, then adding water.

Alternatively, as shown in FIG. 2, the non-halogenated derivative E may be prepared by the salt condensation reaction of the invention, in which the salt B is condensed with the diacid chloride (F), an ester/acid chloride (G) or a diester (H) of squaric acid, followed by hydrolysis of the resultant product J or K to give the derivative E, as shown in FIG. 1. With both the monoacid chloride/monoester G and the diester H, this reaction requires the presence of a base to produce useful yields. However, with the more reactive diacid chloride F, this reaction can be conducted without base.

When the diacid chloride F is used as starting material in this reaction, the intermediate is J, the acid chloride of E, whereas when the diester H is used as starting material, the intermediate is K, the ester of E. When the ester/acid chloride G is used, both J and K are produced, but the production of this mixture poses no problems, since both compounds are readily hydrolyzed to give the derivative E. If desired, the acid chloride J may be treated with methanol to convert it to the ester K, and the latter hydrolyzed to give the derivative E. Acid bromides may be used instead of the acid chlorides, and the group $R^2$ may be varied by changing the 4-substituent on the salt B, as described above. Also, although FIG. 1 shows the use of methyl esters, other ester groups may of course be used.

The acid halides and diesters of squaric acid are known compounds and can readily be prepared by methods known in the art. In addition to the conventional general methods for producing acid halides and esters (for example, reacting squaric acid with 2 equivalents of thionyl chloride in the presence of dimethylformamide), the aforementioned Maahs et al. paper describes the conversion of 2,3,4,4-tetrachloro-cyclobut-2-en-1-one (C) to diesters of squaric acid by reaction with excess alcohol. The paper also describes the conversion of the same compound C to the diacid chloride F by reaction with oleum or sulfur trioxide with boron trioxide or antimony pentachloride as catalyst. Although the mixed ester/acid chloride G does not appear to be described in the literature, it is readily prepared by reacting the diacid chloride F with the stoichiometric amount of the appropriate alcohol.

When a base is used to catalyze the salt condensation reaction, this base is conveniently a tertiary amine, for example triethylamine. The intermediates J and K formed by condensation of F, G or H with one mole of the salt B can react with a second mole of this salt to form an unwanted bispyrylium compound. Accordingly, use of excess salt B should be avoided, for example by adding only the stoichiometric amount of the salt.

The conditions needed for the hydrolysis to produce the derivative E vary depending upon which of the starting materials F, G and H is used. The acid chloride intermediate J can be hydrolyzed simply with water, preferably by heating, whereas the ester intermediate K is preferably hydrolyzed with aqueous mineral acid.

The final step of the synthesis is the dye-forming reaction, condensation of the squaric acid derivative E (FIG. 1) with one mole of the appropriate salt $Q^1CH_2R^1$; the salt J in which $Q^1$ is a 2,6-bis(1,1-dimethylethyl)-pyrylium group is shown in FIG. 1. As already noted, this salt is described in the literature; the corresponding thiopyrylium salt is described in U.S. Pat. No. 4,343,948, issued Aug. 10, 1982 to Kawamura et al. The conditions required for this reaction are substantially the same as those used for the prior art reactions in which two moles of a pyrylium salt are condensed with squaric acid to form a symmetric bispyrylium dye. Thus, this reaction is assisted by base, conveniently a tertiary amine, for example quinoline. The reaction is desirably conducted in solution in an alcohol, conveniently n-butanol. Alternatively, the reaction may be assisted by a Lewis acid, for example titanium tetrachloride in dichloromethane.

Obviously, all the discussion above concerning variations in the 4-substituent and anion of the salt B applies equally to the salt J.

The nomenclature used herein for the Dye A and similar dyes is that used by Chemical Abstracts and is thus apparently that recommended by IUPAC. However, in view of the difficulty of naming the dyes, it is believed that some explanation of this nomenclature may be helpful. A typical dye of the present invention will be written herein as:

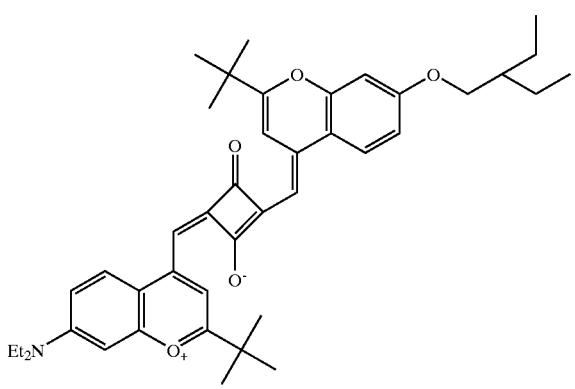

Under substantial neutral conditions, such as in the polymeric binders used in most thermal imaging media, this dye is believed to exist mainly in a zwitterionic form, which is of course a resonance hybrid of the formula given above and:

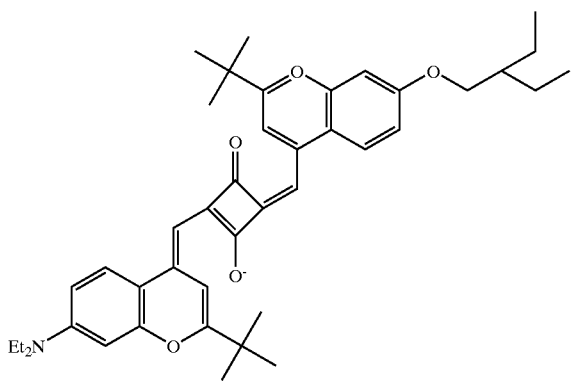

with contributions from other resonance forms. Although the dye is actually isolated in an anhydro form, it is named as the hypothetical hydroxide:

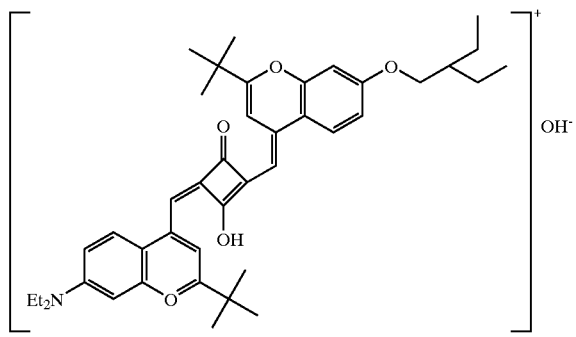

and is thus named 4-[[3-[7-(2-ethylbutoxy)-2-(1,1-dimethylethyl)-(benz[b]-4H-pyran-4-ylidene)methyl]-2-hydroxy-4-oxo-2-cyclobuten-1-ylidene]lmethyl]-7-diethylamino-2-(1,1-dimethylethyl)-benz[b]pyrylium hydroxide inner salt.

A synthesis of salt B by one process of the present invention is shown in FIG. 3 of the accompanying drawings. Although the salt B shown in FIGS. 1 and 2 is the 2,6-bis (1,1-dimethylethyl) salt, for ease of comprehension FIG. 2 shows the general synthesis of the 2,6-di-$R^3$ salt.

In this synthesis, an $R^3$-acetylene M is reacted with a formate ester in the presence of a base, preferably a Grignard reagent, to give the corresponding 1,5-di-$R^3$-penta-1,4-diyn-3-ol N, which is then oxidized by any of the standard methods for the oxidation of secondary alcohols to ketones, to produce the corresponding 1,5-di-$R^3$-penta-1,4-diyn-3-one O. Condensation of this ketone with selenourea produces the corresponding 2,6-di-$R^3$-selenopyran-4-one P, which is treated with an organometallic alkylating agent, preferably a Grignard reagent to introduce a —$CH_2R^2$ group and the 4-position, thus yielding the final salt B.

Alternatively, benzpyrylium analogues of the salts B and L required for the synthesis of FIGS. 1 and 2 may be prepared by the routes shown in FIGS. 5 and 6. In the route shown in FIG. 5, an appropriate ester T of salicylic acid is reacted with dimethyl sulfoxide in the presence of a base to prepare the corresponding 2-($CH_3$—SO—$CH_2$—CO)-phenol U, which is then condensed with an aldehyde RCHO containing the R substituent desired at the 2-position of the benzpyrylium salt to produce the chromone V. This chromone is converted to the salt W as described above with reference to FIG. 3. The corresponding benzthiopyrylium and benzselenopyrylium salts may be prepared from the thio- and seleno-analogues of the compound T.

The synthetic route shown in FIG. 6 begins from a phenol. This synthetic route is primarily, though not exclusively, intended for the synthesis of 6-alkoxybenzpyrylium salts, for which the appropriate phenol is hydroquinone. The hydroquinone is first condensed with a β-ketoester X, which contains the 2-substituent desired in the final salt, to produce the corresponding 6-hydroxychromone Y; use of a simple phenol rather than a hydroquinone in this reaction will produce a 6-unsubstituted chromone. If a 6-alkoxy salt is desired, the 6-hydroxychromone Y is next reacted with an alkyl halide to form the 6-alkoxy group needed, thus forming the 6-alkoxychromone Z. Finally, the chromone Z may be converted to the corresponding salt (AA) as described above with reference to FIG. 3

FIG. 4 shows an example of the chromone condensation reaction of the present invention. In this reaction, a chromone Q, of the formula $Q^1$=O (the chromone in which $Q^1$ is a 2-t-butylbenzthiopyrylium grouping is shown in FIG. 4), which is analogous to the compound P shown in FIG. 3, is condensed with a 2-$CH_2R^1$ squaric acid monoester R (the butyl ester, which may be prepared by the process described in Liebeskind et al., J. Org. Chem., 53, 2482 (1988), is shown in FIG. 4) to give a monocondensed derivative S, which is analogous to the compound K shown in FIG. 1. This reaction is conveniently conducted by treating the chromone with triflic anhydride and then adding the monoester and a base, conveniently triethylamine. It will be seen that the reaction shown in FIG. 4 allows a chromone to be converted directly to a monocondensed derivative without the need to first prepare the corresponding $Q^1CH_2R^1$ salt analogous to the salt B shown in FIGS. 1 and 2. As with the monoester K shown in FIGS. 1 and 2, the monoester S shown in FIG. 4 is readily hydrolyzed to the corresponding hydroxyl compound by conventional techniques well known to synthetic organic chemists.

The chromones required for the reaction of FIG. 4 and analogous reactions may be produced by any of the synthetic routes described above with reference to FIGS. 3, 5 or 6, or may be produced by the route shown in FIG. 7. In the route of FIG. 7, a 1-alkyne BB, bearing at its 2-position the 2-substituent desired in a benzpyrylium chromone, is treated with ethyl chloroformate to produce an α-alkyne ester CC, which is then condensed with a thiophenol to give a 2-phenylthio-α,β-unsaturated carboxylic acid DD. The acid DD is then cyclized to the corresponding thiochromone EE.

Obviously, if desired this thiochromone can be converted to the corresponding benzthiopyrylium salt by the methods previously described.

FIG. 8 illustrates the aromatic dye-forming reaction of this invention. In this reaction, a squaric acid derivative of Formula II (the derivative FF shown in FIG. 8 has a 2-t-butyl-6-sec-butoxybenzpyrylidene group $Q^1$ and a hydrogen atom as $R^1$) is condensed with an aromatic compound having an electron-donating group. This aromatic compound is desirably an N,N-disubstituted aniline (for example a dialkyl- or dicycloalkylaniline) or other aromatic amine, and diethylaniline (GG) is shown in FIG. 8. The presence of an electron-donating group on the aromatic compound is required; unsubstituted arenes do not undergo the reaction. The conditions required for the aromatic dye-forming reaction are essentially the same as for the salt dye-forming reaction, and the aromatic dye-forming reaction proceeds similarly, with a position of the aromatic ring activated by the electron-donating group (usually the para position with aromatic amines) condensing with the 3-position of the squarylium ring to produce the final dye HH.

Although the invention has been shown in the accompanying drawings and described above with reference to a compound in which $Q^1$ is a pyrylium or benzthiopyrylium nucleus and $Q^2$ is a selenopyrylium nucleus, it will be apparent that both $Q^1$ and $Q^2$ can each independently be any aromatic heterocyclic nucleus such that in the compounds of formulae $Q^1CH_2R^1$ and $Q^2CH_2R^2$ the methylene hydrogens are active hydrogens, so that these methylene hydrogen atoms can undergo the condensations with squaric acid derivatives already described. It is preferred that the atoms of $Q^1$ and $Q^2$, which are bonded directly to the $CR^1$ and $CR^2$ groupings respectively, each be part of an aromatic ring. For example, $Q^1$ and $Q^2$ may each independently be an imidazole, benzimidazole, thiazole, benzthiazole, oxazole, benzoxazole, 2- or 4-pyridinium, 2- or 4-quinolinium or indolinium nucleus. In the presently preferred process at least one, and desirably both, of $Q^1$ and $Q^2$ is a heterocyclic nucleus in which a carbon atom is bonded directly to the carbon atom carrying the group $R^1$, and this carbon atom is not bonded directly to a nitrogen atom. Desirably, at least one, and desirably both, of $Q^1$ and $Q^2$ is a non-nitrogenous eterocyclic nucleus, especially preferred nuclei being pyrylium, thiopyrylium, elenopyrylium, benzpyrylium, benzthiopyrylium and benzselenopyrylium nuclei. Such nuclei can be either the 2- or 4-isomers, although the latter are preferred.

In one preferred group of dyes of Formula I, $Q^1$ and/or $Q^2$ is a 2,6-dialkylpyrylium, -thiopyrylium or -selenopyrylium nucleus, in which each of the alkyl groups contains not more than about 8 carbon atoms, especially those in which $Q^1$ and/or $Q^2$ is a 2,6-di-tertiary butylpyrylium, -thiopyrylium or -selenopyrylium nucleus. The presence of these nuclei in the dyes has been found to provide good solubility in polymeric media and high extinction coefficients.

Another preferred group of dyes of Formula I are those in which $Q^1$ and/or $Q^2$ is a 4-benzpyrylium, 4-benzthiopyrylium or 4-benzselenopyrylium nucleus, desirably such a nucleus which carries at its 2-position a substituent in which a non-aromatic carbon atom is bonded directly to the benzpyrylium nucleus, subject to the proviso that if this 2-substituent contains an aromatic nucleus, this aromatic nucleus is not conjugated with the benzpyrylium nucleus. The 2-substituent may be, for example:

a. an alkyl group, for example an isopropyl, sec-butyl, tert-butyl, 2-ethyl-2-methylbutyl or 2,2-dimethylbutyl group;
  b. an alkenyl group, for example a vinyl group;
  c. an alkynyl group, for example an ethine group;
  d. a cycloalkyl group, for example a cyclohexyl group;
  e. a cycloalkenyl group, for example a cyclohexenyl group;
  f. a polycyclic saturated hydrocarbon group, for example a decalinyl or adamantyl group;
  g. a polycyclic, ethylenically unsaturated hydrocarbon group, for example a 6,6-dimethylbicyclo[3.1.1]hept-2-en-2-yl or bicyclo[2.2.1]hept-2-en-5-yl group;
  h. any of the foregoing substituents substituted with aryl, halo, cyano, amino or oxo groups, or containing ether, amine or urethane linkages. The 2-substituent is desirably one in which the carbon atom directly attached to the benzpyrylium nucleus carries not more than one hydrogen atom.

The benzpyrylium nucleus may also carry at its 7-position a substituent in which an element of Group 5A, 6A or 7A of the Periodic Table is directly connected to the benzpyrylium nucleus, subject to the proviso that when this element is of Group 5A or 6A, the 7-substituent may be at least one saturated ring containing this element of Group 5A or 6A, this saturated ring optionally being fused to the phenyl ring of the associated benzpyrylium nucleus. Preferred 7-substituents are alkoxy groups containing not more than about 12 carbon atoms, or disubstituted amino or disubstituted phosphino groups, wherein each of the substituents on the or each disubstituted group comprises an alkyl group containing not more than about 6 carbon atoms, or the two substituents on any one disubstituted group together form, with the nitrogen or phosphorus atom thereof, a heterocyclic ring system, this ring system optionally being fused to the benzpyrylium nucleus which carries the disubstituted amino or phosphino substituent. Examples of suitable 7-substituents include dialkylamino wherein each of the alkyl groups contains not more than about 4 carbon atoms, piperidino, indolinyl, morpholino and $—N[—(CH_2)_3—]_2$ groups, subject to the proviso that when one or both of the amino groups is an $—N[—(CH_2)_3—]_2$ group, the ends of the trimethylene groups remote from the nitrogen atom are joined to the 6- and 8-positions of the benzpyrylium nucleus carrying the nitrogen atom, so that the $—N[—(CH_2)_3—]_2$ group and the benzene ring of the benzpyrylium nucleus together form ajulolidine ring system. As described in the aforementioned Applications U.S. Ser. Nos. 07/616,639 and 07/795,038, dyes containing such 4-benzpyrylium nuclei have desirable properties, including solubility in polymeric media and high extinction coefficients.

Alternatively, the or each benzpyrylium nucleus may carry at its 6-position an alkoxy, alkenyloxy or alicyclyloxy group; the alkyl, cycloalkyl or alicyclic portion of this group may be any of the groups (other than alkynyl) mentioned above as the 2-substituent. Desirably the 6-substituent is an alkoxy or cycloalkoxy group, preferably a branched chain alkoxy group. Specific preferred branched chain alkoxy groups are propoxy, but-2-oxy and 2-ethylbutoxy groups. Preferably, the benzene ring of the benzpyrylium nucleus bears no substituents other than the 6-substituent. It has been found that providing such a branched-chain 6-substituent increases the solubility of the dye in polymeric media. In addition, providing a 6-alkoxy substituent moves the wavelength of maximum infra-red absorption approximately 20 nm to longer wavelengths, and thus may be useful in "tuning" the dyes for for use in certain applications. It is believed (although the invention is in no way limited by this belief) that the advantageous solubility properties of these 6-substituted dyes are due at least in part to the 6-substituent extending out of the plane of the aromatic nucleus to which it is attached, and thus the choice of a 6-substituent may be influenced by the stereochemistry of the substituent, not merely its chemical nature.

The acid-generating process described in the aforementioned application Ser. No. 07/965,161 makes demands upon the properties of infra-red dyes which differ from those made in the thermal processes described in the aforementioned U.S. Pat. Nos. 4,602,263 and 4,826,976. In the thermal processes, the dye serves simply to absorb infra-red radiation and generate heat in the imaging medium. For the dye to fulfil these functions effectively, it is desirable that (a) the dye be soluble in the polymers typically used as binders in imaging media; (b) the dye not aggregate substantially at the concentration employed; (c) the dye have low visible absorption; (d) the dye be thermally stable; and (e) the dye not fluoresce in the binder; provided the dye has no adverse effects on any of the other components of the color-forming layer in which it is present, the chemical properties of the dye are not generally important. Although solubility of the dye in the polymer and aggregation therein will of course vary with the specific polymer used, empirically it has been found that dye solubility and low visible absorption are associated with $Q^1$ and/or $Q^2$ being a benzpyrylium nucleus (or a benzthio- or benzseleno-analogue) having a bulky alkyl group (for example tertiary butyl) at the 2-position, and a bulky alkoxy group (for example sec-butoxy) at the 6- or 7-position. Asymmetry of the dye helps to reduce aggregation.

However, in the acid-generating process of the aforementioned application Ser. No. 07/965,161, the choice is more complicated, because it is also necessary to take account of the chemical properties of the dye. In the acid-generating process, it appears that one crucial step is excitation of the dye by absorption of infra-red radiation, followed by transfer of an electron from the excited dye molecule to an electron acceptor, typically a superacid precursor; further reactions by the electron acceptor then generate a strong acid. The electron transfer reaction competes with various processes which return an excited dye molecule to its ground state without electron-transfer, while the further reactions by the electron acceptor compete with back electron-transfer, with return of the dye molecule to its ground state. Accordingly, to increase acid generation, it is desirable that the dye have a sufficiently low oxidation potential to provide a favorable free energy change ($\Delta G°$) for electron transfer, and a long excited state lifetime; the latter is important, since the longer the excited state lifetime, the greater the chance that the excited dye molecule will undergo electron-transfer. Empirically, it has been found that favorable $\Delta G°$ and a long excited state lifetime are promoted by dyes containing low atomic weight chalcogens (O>S>Se), and by a 2-alkyl, -cycloalkyl or -orthoalkoxyphenyl substituent on a benzpyrylium nucleus. In addition, these parameters are strongly affected by the nature of the 7-substituent on a benzpyrylium nucleus, the most favorable 7-substituents being morpholino and an —N[(CH$_2$)$_3$—]$_2$ grouping in which the ends of the trimethylene groups remote from the nitrogen atom are joined to the 6- and 8-positions of the nucleus, so that the —N[—(CH$_2$)$_3$—]$_2$ grouping and the benzene ring of the nucleus together form a julolidine ring system. Asymmetric dyes provide greater freedom of choice within the aforementioned constraints.

Although $R^1$ and $R^2$ may be other groups, for example cycloalkyl groups or any of the other aliphatic and cycloaliphatic groups discussed above as potential 2-substituents on benzpyrylium groups $Q^1$ and $Q^2$, it is preferred that these two groups each independently be a hydrogen atom or an alkyl group containing not more than about 6 carbon atoms.

Although the processes of the present invention may be used for the synthesis of both symmetric dyes (when B and L in the drawing are the same, so that in the final dye the groupings $Q^1CR^1$ and $Q^2CR^2$ are the same) or asymmetric dyes (when B and L are different, so that the groupings $Q^1CR^1$ and $Q^2CR^2$ are different), these processes are typically employed to produce asymmetric dyes, since the symmetric dyes can usually readily be prepared by condensing two moles of the appropriate salt with squaric acid. However, there are certain applications (see, for example, the aforementioned U.S. Pat. Nos. 4,602,263 and 4,826,976) which require the use of a plurality of infra-red dyes with absorptions at differing wavelengths. To provide an appropriate set of dyes for such an application, it may be convenient to prepare a single intermediate similar to the compound E in the drawing and then to react this single intermediate with a plurality of differing salts to produce the final dyes. In these circumstances, even though one of the final dyes may be symmetric, it may be convenient to produce this symmetric dye by the same route as the asymmetric dyes.

In the squaric acid derivatives of Formulae II, III, IV, V, VI and VII, the preferred groups $Q^1$ and $R^1$ are as already discussed above with reference to the dyes of Formula I. Of these derivatives in which $Q^1$ is a 2,6-dialkylpyrylium, -thiopyrylium or -selenopyrylium nucleus, those in which A is a chlorine atom, hydroxyl group or an ester grouping formed from such a hydroxyl group with an alkanol containing not more than about 6 carbon atoms, and $R^1$ is a hydrogen atom or an alkyl group containing not more than about 6 carbon atoms, are preferred. Especially preferred are such derivatives in which A is a hydroxyl group and $R^1$ is a hydrogen atom, namely:

1-[[2,6-bis(1,1-dimethylethyl)-4H-pyran-4-ylidene] methyl]-2-hydroxy-cyclobut-1-ene-3,4-dione;

1-[[2,6-bis(1,1-dimethylethyl)-4H-thiopyran-4-ylidene] methyl]--2-hydroxycyclobut-1-ene-3,4-dione; and 1-[[2,6-bis(1,1-dimethylethyl)-4H-selenopyran-4-ylidene]methyl]--2-hydroxycyclobut-1-ene-3,4-dione.

Another preferred derivative of Formula VI is that in which A is a hydroxyl group and $R^1$ is a hydrogen atom, but $Q^1$ is a 2-t-butyl-6-sec-butoxybenzpyrylium group, namely:

4-[[6-[but-2-oxy]-2-[1,1-dimethylethyl]benz[b]-4H-pyran-4-ylidene]methyl]-3-hydroxycyclobut-3-ene-1,2-dione.

The dyes produced by the processes of the present invention may be used in any of the applications in which prior art near infra-red absorbers have been used. Thus, the dyes may be used as dyes in printing inks intended to provide markings which can be read under near infra-red radiation, for example, on packages of consumer items intended to be scanned by near infra-red laser scanners. At least some of the present dyes may also be useful as charge transfer materials for use in xerography, electrophotography and similar processes, and as laser dyes.

However, because of their high extinction coefficients in the near infra-red region, the dyes produced by the present processes are especially useful in processes for generating heat in a medium; in such a process at least part of the medium is exposed to near infra-red actinic radiation of a frequency absorbed by the dye, so that the radiation is absorbed by the dye and heat is generated within the parts of the medium exposed to the radiation. Typically, in such a process, the radiation is provided by a laser. The medium may also comprise a thermally sensitive material capable of undergoing a color change upon exposure to heat; the medium is exposed imagewise to the radiation, and the heat generated by the dye is sufficient to effect a color change in the thermally sensitive material, so that an image is formed in the medium. Thus, for example, the present dyes may be used as the near infra-red absorbers in the thermal imaging processes described in the aforementioned U.S. Pat. Nos. 4,602,263 and 4,826,976, which rely upon the irreversible unimolecular fragmentation of one or more thermally unstable carbamate moieties of an organic compound to effect a visually discernible color shift from colorless to colored, from colored to colorless or from one color to another. The present dyes may also be used in the similar processes described in U.S. Pat. Nos. 4,623,896; 4,663,518; 4,720,449; 4,720,450; 4,745,046; 4,818,742; 4,839,335; 4,894,358; 4,960,901 and 5,153,169.

In such a process, preferably the thermally sensitive material is originally substantially colorless and is converted by the heat generated to a colored material in exposed areas of the image. Multi-colored images may be produced using a heat-sensitive element containing an imaging layer of colorless imaging compound (leuco dye) for forming a yellow image, an imaging layer of colorless imaging compound for forming a cyan image, and an imaging layer of colorless imaging compound for forming a magenta image. Preferred leuco dyes, and processes for their preparation, are described in U.S. Pat. No. 4,663,518, and other preferred yellow-forming leuco dyes are described in U.S. Pat. No. 5,243,052.

In the production of such multi-color images, each imaging layer contains, besides the leuco dye, an infra-red absorber selected such that the three infra-red absorbers absorb radiation at different predetermined wavelengths above 700 nm sufficiently separated so that each imaging layer may be exposed separately and independently of the others by using infra-red radiation at the particular wavelengths selectively absorbed by the respective infra-red absorbers. As an illustration, the yellow, magenta and cyan precursors may have associated infra-red absorbers that absorb radiation at (say) 760 nm, 820 nm and 880 nm, respectively, and may be addressed by laser sources, for example, infra-red laser diodes emitting radiation at these respective wavelengths so that the three imaging layers can be exposed independently of one another. While each layer may be exposed in a separate scan, it is usually preferred to expose all of the imaging layers simultaneously in a single scan using multiple laser sources of the appropriate wavelengths. Instead of using superimposed imaging layers, the heat-sensitive compounds and associated infra-red absorbers may be arranged in an array of side-by-side dots or stripes in a single recording layer.

As already noted, the present dyes may also be used in the acid-generating imaging process of the aforementioned application Ser. No. 07/965,161.

Alternatively, the present dyes may be used in a thermal imaging process in which the medium comprises one layer of a multi-layer structure, this structure further comprising a support layer disposed on one side of the medium and a colored layer adhering to the opposed side of the medium. In this type of thermal imaging process, the heat generated on exposure of the dye to actinic radiation causes increased adhesion of the colored layer to the support layer, such that upon application of a peeling force to the colored layer, the colored layer will peel from the support layer in areas which have not been exposed to the radiation, but in areas which have been exposed to radiation the colored layer will remain attached to the support layer. A preferred thermal imaging process of this type is described and claimed in International Patent Application No. PCT/US87/03249.

From the foregoing description, it will be seen that the present invention provides processes and intermediates that enable a wide variety of asymmetric infra-red dyes to be synthesized without the need to separate mixtures of asymmetric and symmetric dyes. Because the present dye-forming reaction does not produce the compounds of Formula I admixed with the corresponding symmetric compounds, the present dye-forming reaction can readily produce compounds of Formula I essentially free from squarylium compounds of the formulae:

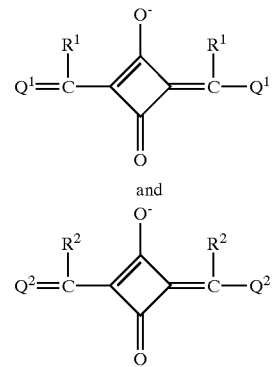

Using the processes of the present invention, syntheses of asymmetric dyes can be carried out in a few steps from readily available starting materials and in good yields.

The following Examples are now given, though by way of illustration only, to show details of particularly preferred reagents, conditions and techniques used in the processes of the present invention.

PART 1: PREPARATION OF STARTING MATERIALS
Part 1.1: Preparation of Chromones and Salts The following Examples 1–44 show methods for the preparation of the chromones P (FIG. 3) and Q (FIG. 4), the salt B (FIGS. 1 and 2) and analogous materials used as starting materials in the processes of the present invention.

EXAMPLE 1

Preparation of 2,6-bis(1,1-Dimethylethyl)-4-methylselenopyrylium tetra-fluoroborate This Example illustrates the preparation of the selenopyrylium salt B ($R^2$=H, $R^3$=1,1-dimethylethyl) by the synthetic route shown in FIG. 3, which uses reactions based upon those described in Liebig's Ann. Chem., (1973), 1583; J. Org. Chem., 27, 1597 (1962) and Tetrahedron, 24, 4285 (1968).

Part A: Preparation of 2,2.8,8-Tetramethylnona-3.6-diyn-5-ol (N)

3,3-Dimethylbut-1-yne (10 g, 122 mmole, available from Aldrich Chemical Company) was dissolved in tetrahydrofuran (150 mL) and the solution was cooled under nitrogen to −60° C. Methyl magnesium chloride (38.0 mL of a 2.9 M solution in tetrahydrofuran, 110 mmole) was added dropwise over a period of 30 minutes, and then the reaction mixture was allowed to warm to room temperature and stirred at room temperature for 16 hours. The resultant clear solution was cooled to −30° C., which resulted in the formation of a thick suspension, and ethyl formate (4.5 niL, 56 mmole) was added dropwise; the resulting reaction was strongly exothermic. After the addition of the ethyl formate had been completed, the reaction mixture was stirred at room temperature for 3 hours, then poured into an ammonium chloride solution and extracted with ether. The ether layer was separated, washed with water, dried over sodium sulfate and evaporated to an oil. Since the proton nuclear magnetic resonance (NMR) spectrum of the oil indicated that tetrahydrofuran was still present, the oil was pumped under high vacuum to give 8.43 g of a solid, which was recrystallized from pentane to yield a first crop of 5.31 g, and a second crop of 2.1 g, of 2,2,8,8-tetramethyl-nona-3,6-diyn-5-ol. The structure of this product was confirmed by FAB mass spectroscopy and by proton NMR spectroscopy.

Part B: Preparation of 2.2,8,8-Tetramethylnona-3.6-diyn-5-one (O)

The 2,2,8,8-tetramethylnona-3,6-diyn-5-ol prepared in Part A (7.0 g, 36 mmole) was dissolved in 150 mL of benzene, cooled to 5–10° C. and nickel peroxide (18.15 g, 200 mmole) was added over a period of 20 minutes. After the addition had been completed, the reaction mixture was stirred at room temperature for 30 minutes, then filtered, and the nickel peroxide left on the filter was washed well with benzene and then with dichloromethane. The filtrate was evaporated to give a yellow solid, which was recrystallized from benzene to give 2,2,8,8-tetramethylnona-3,6-diyn-5-one as pale yellow crystals (4.2 g). The structure of this product was confirmed by fast atom bombardment (FAB) mass spectroscopy.

Part C: Preparation of 2,6-bis(1,1-Dimethylethyl) selenopyran-4-one (P)

Selenourea (2 g, 16.2 mmole) was dissolved under nitrogen in dimethylformamide (3 mL) and the solution was stirred on an ice bath as a solution of the 2,2,8,8-tetramethylnona-3,6-diyn-5-one prepared in Part B (1.03 g, 5.4 mmole) in acetonitrile (5 mL) was added dropwise over a period of 15 minutes. The ice bath was then removed and the reaction mixture stirred at room temperature for 3 hours (a precipitate formed after 2 hours), and then allowed to stand at room temperature overnight. The mixture was filtered and the filtrate reduced in volume by evaporation, then ether (50 mL) was added, whereupon a white solid precipitated. The resultant mixture was filtered and the ether evaporated from the filtrate. The remaining dimethylformamide solution was treated with ice water (25 mL) to give a gum, which solidified on standing, and was then extracted with hexane. The water layer remaining was decanted and extracted twice with hexanes. The resultant combined hexane solution was combined with the hexane extract of the gum, and the combined hexane solution was washed well with water, then with brine, dried over sodium sulfate and evaporated to dryness. The residue was chromatographed on silica using dichloromethane as eluent, to give 4-(1,1-dimethylethyl)-2-(2,2-dimethyl-propylidene)-2,3-dihydroselenofuran-3-one (952 mg) as the major product. Further elution with ether gave 2,6-bis(1,1-dimethylethyl) selenopyran-4-one (300 mg, 20% yield based on the acetylenic starting material). The structure of this product was confirmed by FAB mass spectroscopy and by proton NMR spectroscopy.

Part D: Preparation of Salt (B)

The 2,6-bis(1,1-dimethylethyl)-selenopyran-4-one prepared in Part C (218 mg, 0.80 mmole) was dissolved in tetrahydrofuran (5 mL, dried over lithium aluminum hydride) under nitrogen and cooled to 0° C. as methyl magnesium chloride (415 μL of a 2.9 M solution in tetrahydrofuran, 1.20 mmole) was added dropwise. The mixture was stirred at 0° C. for 15 minutes, and then for a further 1.5 hours as it was allowed to warm to room temperature, poured into saturated ammonium chloride solution, and the resultant mixture extracted several times with ether. The separated ether extracts were combined and evaporated to yield a crude oil containing the 4-hydroxy-4-methyl-4H-selenopyran intermediate. This oil was dissolved in ethanol and several drops of tetrafluoroboric acid were added with swirling. The resultant mixture was warmed briefly, then evaporated to dryness and partitioned between dichloromethane and water. The dichloromethane layer was dried over sodium sulfate and evaporated to dryness. Trituration with ether gave 2,6-bis(1,1-dimethylethyl)-4-methylselenopyrylium tetrafluoroborate (86 mg, 30% yield based on the selenopyranone starting material) as pale green-grey crystals. The structure of this product was confirmed by FAB mass spectroscopy.

EXAMPLE 2

Preparation of 2,6-bis(1,1-Dimethylethyl)-4-methylselenopyrylium tetra-fluoroborate This Example illustrates an improved preparation of the same salt B as in Example 1 above.

Part A: Preparation of 2,2,8.8-Tetramethylnona-3,6-diyn-5-ol (N)

Methyl magnesium chloride (1 L of a 3M solution in tetrahydrofuran, 3 mole) was added dropwise over a period of 45 minutes to a solution of 3,3-dimethylbut-1-yne (250 g, 3.04 mol) in dry tetrahydrofuran (750 mL) at −30° C. under nitrogen. The cold bath was removed and the reaction mixture was stirred at room temperature overnight. The resultant solution was then cooled to −10° C. and ethyl formate (116 g of material of 97% purity, 1.5 mol) was added dropwise over a period of 30 minutes. The solution was allowed to attain room temperature and stirred at room temperature for 4 hours, then poured into a mixture of ice/water (5L) and acetic acid (500 mL). The resultant mixture was extracted with heptanes (200 mL), the organic layer removed, and the aqueous layer extracted with additional heptanes (200 mL). The combined organic layers were washed with cold water, dried over anhydrous magnesium sulfate, filtered and placed in a freezer overnight. The resultant crystals were collected by filtration, washed with cold petroleum ether and air-dried to yield 2,2,8,8-tetramethylnona-3,6-diyn-5-ol (162 g, 56% yield). By allowing the filtrate to evaporate and stirring the residue with cold petroleum ether (at −20° C.), an additional 5% yield of the alcohol may be recovered. The structure of this compound was confirmed by mass spectroscopy and by $^1$H and $^{13}$C NMR spectroscopy.

Part B: Preparation of 2.2,8.8-Tetramethylnona-3.6-diyn-5-one (O)

For this step in the synthesis, Jones' Reagent was prepared by adding concentrated sulfuric acid (598 g) to a solution of sodium dichromate dihydrate (440 g, 1.47 mole) in water (1320 mL) and diluting the resultant solution with water (to a volume of 2200 mL).

The Jones' reagent (2.2 L) was added dropwise to a solution of 2,2,8,8-tetramethylnona-3,6-diyn-5-ol (500 g, 2.6 mol, prepared in Part A above) in acetone (1.5 L), and the rapid, exothermic reaction which followed was monitored by thin layer chromatography for disappearance of starting material. When this had been observed, the two-phase mixture was poured with agitation into ice/water, and the resultant precipitate was filtered and washed with water until a colorless filtrate was obtained. Air drying afforded 2,2,8, 8-tetramethylnona-3,6-diyn-5-one (471 g, 94% yield) as pale yellow crystals which melted at 65–66° C. The structure of this compound was confirmed by mass spectroscopy and by $^1$H and $^{13}$C NMR spectroscopy.

Part C: Preparation of 2,6-bis(1,1-Dimethylethyl) selenopyran-4-one (P)

Lithium triethylborohydride (Super Hydride, available from Aldrich Chemical Company, Milwaukee, Wisconsin, 400 mL of a 1M solution in tetrahydro-furan) was added to selenium powder (16 g, 0.2 mole) under nitrogen. The temperature of the mixture was observed to rise to 45° C. The milky white resultant solution was stirred for 1 hour, after which sodium methoxide (173 g of a 25% solution in methanol) was added and the mixture was cooled to 10° C. Meanwhile, sodium methoxide (108 g of a 25% solution in methanol) was added to a solution of 2,2,8,8-tetramethylnona-3,6-diyn-5-one (38 g, 0.2 mole, prepared in Part B above) in tetrahydrofuran (200 mL) at 5° C. The resultant solution was added dropwise over a 30 minute period to the selenide solution prepared above, this solution being kept below 10° C. throughout the addition. The resultant yellow-brown mixture was stirred overnight at room temperature, then poured into a crushed ice slurry (2.5 gal.) with rapid agitation, and stirred for an additional 90 minutes. The product was filtered, and the solid residue was washed with cold water and air dried to afford a brown granular material, which was subjected to Soxhlet extraction at reflux with heptanes (150 mL). The resultant brown solution was allowed to cool and stir for 2 hours as crystals began to form. It was then placed in a freezer for 2 days, after which the product was removed by filtration, washed with cold heptane (–30° C.) and air dried to give tan crystals (14.9 g). The filtrate was allowed to evaporate and the brown residue was stirred with cold heptanes (–30° C.). The resulting tan crystals were removed by filtration, washed with cold heptanes and air dried. They were then combined with the first crop to afford 2,6-bis(1,1-dimethylethyl) selenopyran-4-one (23.5 g, 43.5% yield), which melted at 83-84° C.

Part D: Preparation of Salt (B)

Methyl magnesium chloride (40 mL of a 3 M solution in tetrahydro-furan, 0.12 mole) was added to a solution of 2,6-bis[1,1-dimethylethyl]seleno-pyran-4-one (22 g, 0.081 mole, prepared in Part C above) in dry tetrahydrofuran (100 mL) which was initially maintained at –20° C. using a cold bath; the addition was effected at such a rate that the temperature in the reaction vessel did not exceed –15° C. The cold bath was removed, and the pale yellow solution was allowed to stir at room temperature for four hours, during which time a thick slurry formed. The mixture was then poured into ice/water (1 L) with rapid agitation, and tetrafluoro-boric acid (200 mL of a 48% aqueous solution) was added. Stirring was continued for a further two hours, after which the mixture was extracted with dichloromethane (3×100 mL). The organic layer was dried over magnesium sulfate and concentrated under reduced pressure to give a tan residue, which was triturated with ether. The resultant solid was collected by filtration, washed with ether and dried to give 2,6-bis(1,1-dimethylethyl)-4-methylselenopyrrylium tetrafluoroborate (24.7 g, 85% yield) as an off-white solid melting at 65–66° C. The structure of this compound was confirmed by mass spectroscopy and by $^1$H and $^{13}$C NMR spectroscopy.

EXAMPLE 3

Preparation of 4-Diethylamino-2-hydroxy-2'-(methylsulfonyl)aceto-phenone

This Example illustrates the reaction T→U shown in FIG. 5. The procedure followed is analogous to that described in Von Strandtmann et al., J. Het. Chem., 9, 171 (1972).

Sodium hydride (2 g of a 50% dispersion in mineral oil, 0.042 mole) was added to dry dimethyl sulfoxide (25 mL). The resultant mixture was stirred at 60–70° C. under nitrogen until hydrogen evolution ceased (approximately 1 hour). The solution was then cooled to 50° C. and a solution of methyl 4-diethylamino-salicylate (2.23 g, 0.01 mole) in toluene (25 mL) was added over a period of 5 minutes. The resultant solution was stirred at 40–50° C. for 3 hours, then cooled to 20° C. and allowed to stand for 17 hours. The mixture was then poured into ice/water (150 mL) containing conc. hydrochloric acid (5 mL). Toluene (25 mL) was added and the mixture was extracted. The toluene layer was separated, washed with brine, dried over sodium sulfate and evaporated to afford the crude product as a yellow oil. Trituration with ether produced purified 4-diethylamino-2-hydroxy-2'-(methylsulfonyl)acetophenone (1.6 g, 59% yield) as a waxy brown solid, melting point 91–92° C. The structure of this compound was confirmed by mass spectroscopy and by $^1$H and $^{13}$C NMR spectroscopy.

EXAMPLES 4–7

Preparation of Additional Substituted Acetophenones

The following substituted acetophenones were prepared in a manner exactly analogous to that used in Example 3 above.

EXAMPLE 4

2-Hydroxy-2'-[methylsulfonyl]acetophenone

This compound was prepared from methyl salicylate and dimethyl sulfoxide.

EXAMPLE 5

3-Isopropyl-2-hydroxy-6-methyl-2'-[methylsulfonyl]-acetophenone

This compound was prepared from methyl 3-isopropyl-6-methyl-salicylate and dimethyl sulfoxide.

EXAMPLE 6

6-Isopropyl-2-hydroxy-3-methyl-2'-[methylsulfonyl]-acetophenone

This compound was prepared from methyl 6-isopropyl-3-methyl-salicylate and dimethyl sulfoxide.

EXAMPLE 7

4-[Pent-3-oxy]-2-hydroxy-2'-[methylsulfonyl] acetophenone

This compound was prepared from methyl 4-[pent-3-oxy] salicylate and dimethyl sulfoxide.

The methyl 4-[pent-3-oxy]salicylate used was prepared as follows. A mixture of methyl 4-hydroxysalicylate (74 g, 0.44 mole), 3-bromopentane (80 g, 0.53 mole), potassium iodide (20 g) and potassium carbonate (100 g) in methyl ethyl ketone (MEK, 500 mL) was heated at reflux for 65 hours. The cooled reaction mixture was then filtered and concentrated under reduced pressure. The resultant oily residue was stirred with dilute hydrochloric acid, then extracted into dichloromethane. The dichloromethane solution was washed with brine, dried over anhydrous sodium sulfate and concentrated to a clear liquid (67.0 g, 64% yield). The structure of this compound was confirmed by mass spectroscopy and by $^1$H and $^{13}$C NMR spectroscopy.

EXAMPLE 8

Preparation of 7-Diethylamino-2-phenylbenz-4H-pyran-4-one

This Example illustrates the reaction U→V shown in FIG. 5.

Piperidine (0.1 g) was added to a solution of 4-diethylamino-2-hydroxy-2'-[methylsulfonyl]acetophenone (1.0 g, 3.71 mmole, prepared in Example 3 above) and benzaldehyde (0.50 g, 4.71 mmole) in toluene (50 mL). The resultant light brown solution was heated at reflux for 2 hours under nitrogen, after which a further quantity of benzaldehyde (0.50 g, 4.71 mmole) was added, and heating was resumed for another 2 hours. The solvent was removed under reduced pressure, and the remaining brown oil was triturated first with hexanes and then with ether, yielding the desired chromone as a yellow powder melting at 126–128 ° C. (0.48 g, 44% yield). The structure of this compound was confirmed by mass spectroscopy and by $^1$H and $^{13}$C NMR spectroscopy. The substituents on this chromone are listed in Table 2 below.

EXAMPLES 9–22

Preparation of Additional Substituted Chromones

The following chromones were prepared in a manner exactly analogous to that used in Example 8 above using the substituted acetophenones of Examples 3–7 above and the aldehydes specified in Table 1 below, which also gives the yield of the reaction. The various substituents present on the chromones, and the yields achieved are given in Table 2 below. All the chromones listed in Tables 1 and 2 were characterized by mass spectroscopy and by $^1$H and $^{13}$C NMR spectroscopy.

TABLE 1

| Example # | Acetophenone of Example # | Aldehyde | Yield % |
|---|---|---|---|
| 9 | 3 | 4-trifluoromethyl-benzaldehyde | 55 |
| 10 | 3 | 4-methoxybenzaldehyde | 69 |
| 11 | 3 | 2-trifluoromethyl-benzaldehyde | 75 (estimated by $^1$H NMR) |
| 12 | 3 | 2,4-dimethyl-benzaldehyde | 53 |
| 13 | 3 | 2-(hex-1-yloxy)-benzaldehyde | 63 |
| 14 | 4 | 2-trifluoromethyl-benzaldehyde | 59 |
| 15 | 4 | 2-(hex-1-yloxy)-benzaldehyde | 82 |
| 16 | 4 | 4-t-butylbenzaldehyde | 66 |
| 17 | 4 | 2-(oct-1-yl)benzaldehyde | 66 |
| 18 | 4 | 2-furaldehyde | 64 |
| 19 | 4 | 2-pyridinecarboxaldehyde | 31 |
| 20 | 5 | 3-benzyloxybenzaldehyde | 89 |
| 21 | 6 | 3-benzyloxybenzaldehyde | 61 |
| 22 | 7 | benzaldehyde | 77 |

TABLE 2

| | Example # | | | | | |
|---|---|---|---|---|---|---|
| | 8 | 9 | 10 | 11 | 12 | 13 |
| Phenyl substituents | | | | | | |
| Ortho | H | H | H | $CF_3$ | $CH_3$ | $OC_6H_{13}$ |
| Meta | H | H | H | H | H | H |
| Para | H | $CF_3$ | $OCH_3$ | H | $CH_3$ | H |
| Benzpyrylium Substituents | | | | | | |
| 5-Position | H | H | H | H | H | H |
| 6-Position | H | H | H | H | H | H |
| 7-Position | $NEt_2$ | $NEt_2$ | $NEt_2$ | $NEt_2$ | $NEt_2$ | $NEt_2$ |
| 8-Position | H | H | H | H | H | H |

| | Example # | | | | | |
|---|---|---|---|---|---|---|
| | 14 | 15 | 16 | 17 | 18 | 19 |
| Phenyl substituents | | | | | | |
| Ortho | $CF_3$ | $OC_6H_{13}$ | H | $CF_3$ | None | None |
| Meta | H | H | H | H | — | — |
| Para | H | H | $t-C_4H_9$ | $n-C_8H_{17}$ | Unsub. furan group in place of phenyl | Unsub. pyridino group in place of phenyl |
| Benzpyrylium Substituents | | | | | | |
| 5-Position | H | H | H | H | H | H |
| 6-Position | H | H | H | H | H | H |
| 7-Position | H | H | H | H | H | H |
| 8-Position | H | H | H | H | H | H |

| | Example # | | |
|---|---|---|---|
| | 20 | 21 | 22 |
| Phenyl substituents | | | |
| Ortho | H | H | H |
| Meta | $OCH_2Ph$ | $OCH_2Ph$ | H |
| Para | H | H | H |
| Benzpyrylium Substituents | | | |
| 5-Position | $CH_3$ | $i-C_3H_7$ | H |
| 6-Position | H | H | H |
| 7-Position | H | H | $OCHEt_2$ |
| 8-Position | $i-C_3H_7$ | $CH_3$ | H |

EXAMPLE 23

Preparation of 7-Diethylamino-4-methyl-2-phenylbenzpyrylium tetra-fluoroborate

This Example illustrates the reaction V→W shown in FIG. 5.

Methyl magnesium bromide (3.5 mL of a 3.0 M solution in ether, 10 mmole) was added dropwise over a period of 10 minutes to a solution of 7-diethylamino-2-phenylbenz-4H-pyran-4-one (1.0 g, 3.41 mmole, prepared in Example 8 above) in dry tetrahydrofuran (THF, 25 mL) at 0C under nitrogen. The orange solution was allowed to warm to room temperature and stirred for 17 hours, after which time it was poured into ice/water (200 mL) containing tetrafluoroboric acid (10 mnL of a 50% aqueous solution). A red precipitate formed, which was collected, washed with water and dried to afford the desired salt (1.21 g, 94% yield). The structure of this compound was confirmed by mass spectroscopy and by $^1$H and $^{13}$C NMR spectroscopy.

EXAMPLES 24–35

Preparation of Additional Salts

The following salts were prepared in a manner exactly analogous to that used in Example 23 above using various chromones from Examples 9–22 above, as specified in Table 3 below, which also gives the yield of the reaction. All the chromones listed in Table 3 were characterized by mass spectroscopy and by $^1$H and $^{13}$C NMR spectroscopy, except that in Examples 28 and 34 no $^{13}$C spectra were taken, and in the Examples marked "NP" the salt was not purified but was used "as is" in later work, so that no accurate yield could be calculated, and the salt was characterized by mass spectroscopy only.

TABLE 3

| Example # | Chromone of Example # | Yield of salt, % |
|---|---|---|
| 24 | 9 | 43 |
| 25 | 10 | 66 |
| 26 | 12 | 56 |
| 27 | 13 | NP |
| 28 | 14 | 52 |
| 29 | 16 | 80 |
| 30 | 17 | NP |
| 31 | 20 | NP |
| 32 | 21 | NP |
| 33 | 22 | 93 |
| 34 | 18 | 48 |
| 35 | 19 | 73 |

EXAMPLES 36–41

Synthetic Route of FIG. 6

The following Examples 36–41 illustrate the preparation of the 6-alkoxy chromone Z and the corresponding 6-alkoxy salt AA by the synthetic route shown in FIG. 6, and an analogous reaction.

EXAMPLE 36

Preparation of 6-Hydroxy-2-phenylbenz-4H-pyran-4-one

This Example illustrates the reaction X→Y shown in FIG. 6.

Trifluoromethane sulfonic acid (20 mL) was added dropwise, with stirring, to a mixture of hydroquinone (3.3 g, 0.03 mole) and ethyl 3-oxo-3-phenyl-propanoate (6.3 g, 0.033 mole). The dark red resultant solution was stirred at room temperature for 2 hours, then heated to 60° C. for a further 2 hours, cooled and poured slowly into water (250 mL). The mixture so formed was stirred, and the solid product which precipitated was collected by filtration, washed with water, and recrystallized from methanol (250 mL) to yield the desired chromone as cream-colored platelets (4.2 g, 59% yield). The structure of this compound was confirmed by mass spectroscopy and by $^1$H and $^{13}$C NMR spectroscopy.

EXAMPLE 37

Preparation of 6-[2-Ethylbut-1-oxy]-2-phenylbenz-4H-pyran-4-one

This Example illustrates the reaction Y→Z shown in FIG. 6.

A mixture of 6-hydroxy-2-phenylbenz-4H-pyran-4-one (1.2 g, 5 mmole, prepared in Example 36 above), 1-bromo-2-ethylbutane (1.03 g, 7.5 mmole), potassium carbonate (1.04 g, 7.5 mmole) and sodium iodide (0.75 g, 5 mmole) in MEK (10 mL) was heated for 17 hours at reflux under nitrogen. At this point thin layer chromatography indicated that the reaction was incomplete, so a further quantity of 1-bromo-2-ethylbutane (1.03 g, 7.5 mmole) was added, and heating was resumed for a further 8 hours. To drive the reaction to completion, a final quantity of 1-bromo-2-ethylbutane (1.03 g, 7.5 mmole) was then added, and heating was continued for another 17 hours. The reaction mixture was poured into water (250 mL), and the resultant mixture was acidified using concentrated hydrochloric acid, causing an oil to separate. The mixture was extracted with ether (250 mL aliquots), and the organic layers were washed with water (150 mL), dried over sodium sulfate, and concentrated under reduced pressure to yield the product as a yellowish oil which solidified when scratched (1.6 g). The slightly impure material, whose structure was confirmed by $^1$H and $^{13}$C NMR spectroscopy, was used directly in Example 38 below.

EXAMPLE 38

Preparation of 6-[2-Ethylbut-1-oxy]-4-methyl-2-phenylbenzpyrylium tetrafluoroborate Methyl magnesium bromide (2 mL of a 3M solution in ether, 6 mmole) was added to a solution of 6-[2-ethylbut-1-oxy]-2-phenylbenz-4H-pyran-4-one (0.75 g, 2.5 mmole, prepared in Example 37 above) in THF (7.5 mL) at room temperature. An exothermic reaction accompanied the addition. The reaction mixture was allowed to stand at room temperature for 17 hours, and then poured into a stirred solution of tetrafluoroboric acid (7 mL of an 8M solution, diluted with ice/water (200 mL)). Much foaming was observed, and a yellow/green precipitate was formed. The solid material was collected by filtration, washed with water and air dried to afford the desired salt (0.875 g, 92% yield) as a green powder. The structure of this compound was confirmed by mass spectroscopy and by 1H and $^{13}$C NMR spectroscopy.

EXAMPLE 39

Preparation of 2-[1,1-Dimethylethyl]-6-hydroxybenz-4H-pyran-4-one

This Example illustrates a reaction analogous to X→Y shown in FIG. 6.

Trifluoromethane sulfonic acid (150 g) was added in a slow stream over a period of 30 minutes to a mixture of hydroquinone (30.0 g, 0.272 mole) and methyl 4,4-dimethyl-3-oxopentanoate (48.0 g, 0.304 mole) with ice/water cooling to control the mildly exothermic reaction which ensued. The reaction mixture was then warmed to 50–55° C. and held at that temperature for 3 hours, during which time a red solution developed and, later, some solid material separated. The reaction mixture was then cooled and poured into stirred ice/wvater (1500 mL) containing saturated brine (100 mL), whereupon a gum separated, which solidified with scratching. This material was collected by filtration, washed with water and air-dried to give the desired compound as a pale yellow powder (46.7 g, 79% yield). The structure of this compound was confirmed by mass spectroscopy and by IH and 1$^3$C NMR spectroscopy.

EXAMPLE 40

Preparation of 6-[But-2-oxy]-2-[1,1-dimethylethyl] benz-4H-pyran-4-one

This Example illustrates a reaction analogous to Y→Z shown in FIG. 6.

A mixture of 2-[1,1-dimethylethyl]-6-hydroxybenz-4H-pyran-4-one (25.0 g, 0.115 mole, prepared in Example 39 above), 2-bromobutane (25.95 g, 0.189 mole), potassium carbonate (50.0 g, 0.36 mole) and potassium iodide (20.0 g, 0.12 mole) in MEK (250 mL) was stirred and heated at reflux under nitrogen for 8 hours. A further quantity of 2-bromobutane (8.65 g, 0.063 mole) was then added, and heating was continued for another 16 hours. The mixture was cooled and poured into stirred ice/water (1000 mL) and the mixture so formed was extracted with dichloromethane (2 400 mL aliquots). The combined organic extracts were washed with water (200 mL) and brine (200 mL), dried over magnesium sulfate and concentrated under reduced pressure to give the desired compound as a viscous, golden-brown oil (27.98 g, 89% yield). The structure of this compound was confirmed by mass spectroscopy and by 1H and $^{13}$C NMR spectroscopy.

EXAMPLE 41

Preparation of 6-[But-2-oxy]-2-[1,1-dimethylethyl]-4-methyl-benzpyrylium tetrafluoroborate This Example illustrates a reaction analogous to Z→AA shown in FIG. 6.

Methyl magnesium bromide (100 mL of a 3M solution in ether, 0.3 mole) was added over a period of 20 minutes to a solution of 6-[but-2-oxy]-2-[1,1-dimethylethyl]benz-4H-pyran-4-one (27.22 g, 0.099 mole, prepared in Example 40 above) in dry THF (250 mL) maintained below 10° C. with an ice/water bath; some solid material was observed to separate from the yellow-brown solution. The ice bath was removed, and the reaction mixture was stirred at room temperature for 16 hours. The mixture was then poured cautiously into a rapidly stirred solution of tetrafluoroboric acid (90 mL of a 48% aqueous solution) in ice/water (1000 mL). Vigorous effervescence was observed, and the precipitate which formed was collected by filtration, washed with water, and air-dried to yield the salt as a pale yellow powder (30.08 g, 84% yield). The structure of this compound was confirmed by mass spectroscopy and by 1H and $^{13}$C NMR spectroscopy.

EXAMPLES 42–44

Synthetic Route of FIG. 7

The following Examples 42–44 illustrate the preparation of the 2-tertiary butyl thiochromone EE by the synthetic route shown in FIG. 7.

EXAMPLE 42

Preparation of Ethyl 4.4-dimethvlpent-2-ynoate

This Example illustrates the reaction BB→CC shown in FIG. 7, and is an improved preparation of a compound described in E. A. Halonen, Acta Chem. Scand., 9, 1492–1497 (1955).

t-Butylacetylene (15.38 g, 0.188 mole) was dissolved in tetrahydrofuran (100 mL) in a 500 mL three-necked round-bottomed flask fitted with a nitrogen bubbler, rubber septum and dropping funnel. The resultant solution was cooled to −70° C. using a dry ice/acetone bath, and butyl lithium (72 mL of a 2.5 M solution in hexanes, 0.18 mole) was added dropwise via a syringe. The cooling bath was then removed and the reaction mixture was stirred for 30 minutes, during which time the temperature in the flask rose to 10–15° C. The flask was then again cooled to −70° C. and a solution of ethyl chloroformate (19.5 g, 0.18 mole) was added dropwise. The cooling bath was again removed, and the reaction mixture was stirred for 3 hours. Cold water (75 mL) was next added to quench the reaction, and the aqueous and organic phases were separated. The aqueous phase was extracted with THF (50 mL) and the combined organic phases were washed with 0.1 M hydrochloric acid (75 mL) and brine (100 mL), and dried over magnesium sulfate. Removal of the solvent under reduced pressure afforded a pale yellow oil (28 g) which was distilled under reduced pressure to provide the propiolate ester (23.5 g, 85% yield) as a colorless liquid, which boiled at 70–75° C. at 18–20 mm Hg. The structure of this compound was confirmed by mass spectroscopy and by 1H and $^{13}$C NMR spectroscopy.

EXAMPLE 43

Preparation of 4.4-Dimethyl-3-phenylthiopent-2-enoic Acid

This Example illustrates the reaction CC→DD shown in FIG. 7. This Example and Example 44 are modifications of the methods described in M. R. Detty and B. J. Murray, J. Am. Chem. Soc., 105 883–890 (1983).

A solution of benzenethiol (11 g, 0.1 mole) in methanol (15 mL) was added all at once to sodium methoxide (21.6 g of a 25% methanolic solution, 0.1 mole) with ice/water bath cooling. The reaction mixture was allowed to warm to room temperature for 10 minutes, then cooled again with the ice/water bath. A solution of ethyl 4,4-dimethylpent-2-ynoate (15.4 g, 0.1 mole) in methanol (20 mL) was added all at once, the ice/water bath was removed, and the reaction mixture was held at room temperature for 1 hour. It was then diluted with 95% ethanol (75 mL), and potassium hydroxide (25 mL of a 45% aqueous solution) was added. The reaction mixture was warmed to 50–55° C. using a water bath, and held at this temperature for 1 hour. The reaction mixture was then diluted with water (300 mL) and extracted with carbon tetrachloride (4×50 mL). The aqueous phase was acidified with hydrochloric acid, then extracted with dichloromethane. The dichloromethane layer was dried and concentrated under reduced pressure to yield the desired acid (20 g, 84% yield), which was pure enough to be used without further purification in the following Example. The structure of this compound was confirmed by mass spectroscopy and by $^1$H and $^{13}$C NMR spectroscopy.

EXAMPLE 44

Preparation of 2-[1.1-Dimethylethyl]benz[b]-4H-thiopyran-4-one

This Example illustrates the reaction DD→EE shown in FIG. 7.

Oxalyl chloride (55 mL) was added to crude 4,4-dimethyl-3-phenylthiopent-2-enoic acid (21 g, 89 mmole, prepared in Example 43 above) at 0° C. After the addition was complete, the cooling bath was removed and the reaction mixture was held at room temperature for 30 minutes. Excess oxalyl chloride was then removed under reduced pressure. The residue was dissolved in dichloromethane (150 mL) and the solution was cooled to −78° C. Aluminum chloride (13.4 g, 0.1 mole) was added in one portion, the cooling bath was removed, and the reaction mixture was stirred at room temperature for 1 hour. The reaction was quenched by pouring into ice/water. The organic phase was separated, washed with brine, dried over anhydrous magnesium sulfate and concentrated under reduced pressure. The crude product was recrystallized from hexanes to give the thiochromone (14.1 g, 73% yield). The structure of this compound was confirmed by mass spectroscopy and by $^1$H and $^{13}$C NMR spectroscopy.

Part 1.2 : Preparation of Monoester Monoacid Chloride

The following Examples 45 and 46 show methods for the preparation of the monoester monoacid chloride G (FIG. 2) used as a starting material in the processes of the present invention.

EXAMPLE 45

Preparation of 3-Chloro-4-methoxvygclobut-3-ene-1,2-dione

Thionyl chloride (476 mg, 4.0 mmole) was added to a suspension of 3-hydroxy-4-methoxycyclobut-3-ene-1,2-dione (500 mg, 3.9 mmole, prepared as described in Schmidt, A. H., Synthesis, 1980, 963 and Cohen S. and Cohen, S. G., J. Am. Chem. Soc., 88, 1533 (1966)) and dimethylformamide (0.2 mL) in toluene (5 mL) and the mixture was heated at reflux for one hour to produce an orange solution. The solvent was evaporated and the residue was dissolved in dichloromethane, washed with water, dried over magnesium sulfate and concentrated under reduced pressure. The crude product so obtained was purified by preparative thin-layer chromatography on silica gel with dichloromethane as eluent to give the monoester monoacid chloride (41 mg, 7% yield) as a white solid melting at 47–48° C. The structure of this compound was confirmed by mass spectroscopy and by $^1$H and $^{13}$C NMR spectroscopy.

EXAMPLE 46

Preparation of 3-Chloro-4-methoxvcyclobut-3-ene-1,2-dione

This Example illustrates an alternative preparation of the same compound as Example 45.

Methanol (32 mg, 1.0 mmole) was added to a solution of 3,4-dichloro-cyclobut-3-ene-1,2-dione (151 mg, 1.0 mmole, prepared as described in Schmidt, A. H., Synthesis, 1980, 963) in dichloromethane (0.5 mL) and the resultant solution was allowed to stand at room temperature for 8 hours. The solvent was then removed and the crude product was purified by filtration through silica gel with dichloro-methane as eluent to give the monoester monoacid chloride as a white, crystalline solid (110 mg, 75% yield). This material was identical, by $^{13}$C NMR spectroscopy, to the material prepared in Example 45 above.

PART 2: PREPARATION OF MONOCONDENSED DERIVATIVES

The following Examples 47–63 show methods for the preparation of the monocondensed intermediates D, E, J and K (FIGS. 1 and 2) and analogous compounds by reactions of the present invention.

Part 2.1: Trihalosquaric Formation and Hydrolysis Reactions

Part 2.1.1: Trihalosquaric Formation Reaction

The following Examples 47–51 show the reaction B+C→D shown in FIG. 1, and analogous reactions.

EXAMPLE 47

Preparation of 3-[2.6-di(1,1-Dimethylethyl)-(4H-pyran-4-ylidene)-methyl]-2,4,4-trichlorocyclobut-2-en-1-one This Example illustrates the preparation, by a reaction analogous to B+C→D shown in FIG. 1, of the trichlo- rosquaric acid derivative of Formula III in which $Q^1$ is a 2,6-bis(1,1-dimethylethyl)-4-pyrylidene grouping, $R^1$ is a hydrogen atom, and each group X is a chlorine atom.

2,6-Bis(1,1-dimethylethyl)-4-methylpyrylium trifluoromethane sulfonate (8.0 g, 22.4 mmole, prepared as described in Organic Syntheses, 60, 34–39) and dried Baker ANGA-542 basic resin (40 g, 59.2 meq) were stirred in tetrahydrofuran (300 mL), then 2,3,4,4-tetrachlorocyclobut-2-en-1-one (4.6 g, 3.1 mL, 22.4 mmole, prepared as described in R. C. DeSelms, C. J. Fox, R. C. Riordan, Tetrahedron Letters, 1970, 781; this paper also describes a preparation of the diacid chloride F shown in FIG. 2) was added all at once. The resultant reaction mixture was stirred for a further 4 hours; the color, which had been green after the addition of the tetrachloro compound, gradually changed to orange-brown. The reaction mixture was then filtered, the solvent removed until the residue was almost dry, and the residue recrystallized from boiling toluene to give the trichlorosquaric acid derivative as a yellow, crystalline solid, which gave only a single spot upon thin layer chromatography on silica gel with dichloromethane as eluent. The structure of the product was confirmed by fast atom bombardment (FAB) mass spectroscopy and by proton NMR spectroscopy. The infra-red spectrum of the product showed bands at 2950, 1770, 1650, 1540 (broad), 1310, 1250, 1200, 940 and 800 cm$^1$.

EXAMPLE 48

Preparation of 3-[2,6-bis(1,1-Dimethylethyl)-(4H-selenopyran-4-ylidene)methyl]-2,4,4-trichlorocyclobut-2-en-1-one This Example illustrates the preparation, by the reaction B+C→D shown in FIG. 1, of the trichlorosquaric acid derivative of Formula InI in which $Q^1$ is a 2,6-bis(1,1-dimethylethyl)-4-selenopyrylidene grouping, $R^1$ is a hydrogen atom, and each group X is a chlorine atom.

A 500 mL three-necked round-bottom flask was equipped with a magnetic stirrer, a dropping funnel with a pressure-equalizing side arm, a condenser with a dry nitrogen gas inlet tube and an outlet attached to a succession of scrubbers containing 10% aqueous sodium hydroxide and 10% aqueous lead acetate. Into this flask were placed 2,6-bis(1,1-dimethylethyl)-4-methyl-selenopyrylium tetrafluoro-borate (3.0 g, 8.4 mmole, prepared as in Example 1 above, 2,3,4, 4-tetrachloro-cyclobut-2-en-1-one (1.7 g, 8.4 mmole) and dichloromethane (150 mL). Stirring was begun and a solution of triethylamine (2.3 mL, 16 mmole) in dichloromethane (50 mL) was added dropwise over a period of 1.5 hours under nitrogen. After the addition of the triethylamine had been completed, the reaction mixture was stirred at room temperature for an additional 1.5 hours, then filtered through a sintered glass funnel containing silica gel (40 g). The silica gel was washed several times with small portions of dichloromethane until the washings were pale orange. The filtrate and washings were combined and evaporated to dryness on a rotary evaporator on a water bath kept at approximately 40° C. The residual green mass was triturated with hexane (60 mL) until maroon crystals formed; these crystals were removed by suction filtration and dried in vacuo at approximately 30° C. to yield 3-[2,6-bis(1,1-dimethylethyl)-(4H-selenopyran-4-ylidene)methyl]-2,4,4-trichlorocyclo-but-2-en-1-one (2.2 g, 60% yield).

EXAMPLE 49

Preparation of 3-[2.6-bis(1.1-dimethylethyl)-(4H-selenopyran-4-ylidene)methyl]-2,4,4-trichlorocyclobut-2-en-1-one This Example illustrates an improved preparation of the same trichlorosquaric acid derivative of Formula III as in Example 48 above.

A solution of triethylamine (14.8 g, 147 mmole) in dichloromethane (40 mL) was added dropwise under nitrogen to a solution of 2,6-bis(1,1-dimethyl-ethyl)-4-methylselenopyrylium tetrafluoroborate (26.2 g, 73.4 mmole, prepared in Examples 1 and 2 above) and 2,3,4,4-tetrachlorocyclobut-2-en-1-one (15.2 g, 73.4 mmole) in dichloromethane (60 mL), contained in a flask equipped with a condenser and an outlet connected to a gas-washing bottle containing 10% aqueous sodium hydroxide solution; the addition was effected at a rate such that the temperature of the reaction mixture did not exceed 35° C. After the addition had been completed, the reaction mixture was stirred for one hour, then applied to a column packed with silica gel. Elution with dichloromethane, followed by evaporation of the solvent under reduced pressure, provided the crude product, which was further purified by trituration with trifluoroethanol for one hour to give 3-[[2,6-bis(1,1-dimethylethyl)-4H-selenopyran-4-ylidene]methyl]-2,4,4-trichlorocyclo-but-2-en-1-one (23 g, 71% yield) as maroon crystals. The structure of this compound was confirmed by mass spectroscopy and by $^1$H and $^{13}$C NMR spectroscopy.

EXAMPLE 50

Preparation of 2-Chloro-3-[3-ethyl-5-fluorobenzothiazol-2-ylidene]-methyl-4,4-dichlorocvclobut-2-en-1-one This Example illustrates the preparation, by a reaction analogous to B+C→D shown in FIG. 1, of the trihalosquaric acid derivative of Formula III in which $Q^1$ is a 3-ethyl-5-fluorobenzothiazole nucleus, $R^1$ is a hydrogen atom and each group X is a chlorine atom.

Triethylamine (65 mg, 0.64 mmole) was added dropwise over a period of 1 minute to a solution of 3-ethyl-5-fluoro-2-methylbenzothiazolium p-toluene-sulfonate (235 mg, 0.64 mmole, prepared as described in U.S. Pat. No. 4,387,155) and 2,3,4,4-tetrachlorocyclobut-2-en-1-one (100 mL) in dimethylformamide (2 mL). After standing for two hours at room temperature, the reaction mixture was poured onto ice and extracted with dichloromethane. The organic phase was washed with water, dried and concentrated under reduced pressure. The crude residue was purified by preparative thin layer chromatography on silica gel with dichloromethane as eluent to give the trihalosquaric acid derivative (30 mg, 13% yield). The structure of this compound was confirmed by mass spectroscopy and by $^1$H NMR spectroscopy.

EXAMPLE 51

Preparation of 3-[2.6-bis(1,1-Dimethylethyl)-(4H-thiopyran-4-ylidene)-methyl]-2,4,4-trichlorocyclobut-2-en-1-one This Example illustrates the preparation, by a reaction analogous to B+C→D shown in FIG. 1, of the trihalosquaric acid derivative of Formula III in which $Q^1$ is a 2,6-bis(1,1-dimethylethyl)-4-thiopyrylidene grouping, $R^1$ is a hydrogen atom and each group X is a chlorine atom.

Triethylamine (834 mg, 8.26 mmole) was added in three portions, over a period of ten minutes, to a solution of 2,3,4,4-tetrachlorocyclobut-2-en-1-one (850 mg, 4.13 mmole) and 2,6-bis(1,1-dimethylethyl)-4-methylthiopyrylium tetra-fluoroborate (1.28 g, 4.13 mmole, prepared as described in U.S. Pat. No. 4,343,948) in dichloromethane (6 mL). An immediate exotherm to reflux accompanied each addition. The reaction mixture was stirred at 20° C. for 1.5 hours, then passed through a 30×70 mm silica gel pad eluted with dichloromethane. The fractions containing most of the desired product were concentrated under reduced pressure to give a brown solid (1.04 g) which was triturated with trifluoroethanol (1.5 mL) to provide bright red needles, which were collected and dried to 626 mg (39% yield), melting point 189–191° C. Evaporation of additional chromatographic fractions provided (after trituration with trifluoroethanol) a second crop (142 mg, 9% yield). The structure of this compound was confirmed by mass spectroscopy and by $^1$H NMR spectroscopy.

Part 2.1.2: Hydrolysis Reaction

The following Examples 52–54 show the reaction D→E shown in FIG. 1, and analogous reactions.

EXAMPLE 52

Preparation of 3-[2.6-bis(1,1-Dimethylethyl)-(4H-pyran-4-ylidene)-methyl]-4-hydroxycyclobut-3-ene-1,2-dione This Example illustrates the preparation, by a reaction analogous to D→E shown in FIG. 1, of the squaric acid derivative of Formula II in which $Q^1$ is a 2,6-bis(1,1-dimethylethyl)-4-pyrylidene grouping and $R^1$ is a hydrogen atom. 3-[2,6-Bis(1,1-dimethylethyl)-(4H-pyran-4-ylidene)-methyl]-2,4,4-tri-chlorocyclobut-2-en-1-one (100 mg, 0.27 mmole, prepared in Example 47 above), was dissolved in triflic acid (1 mL) and the resultant solution heated at 60° C. for 1 hour, 80° C. for a further 2 hours, and finally at 105° C. for 5 hours. The hot mixture was then poured over ice, and the resultant mixture stirred to give a solid precipitate. The mixture was extracted several times with dichloromethane, and the extracts were combined, washed with brine, dried over sodium sulfate and evaporated to dryness. The residue was redissolved in dichloromethane and applied to two preparative silica gel chromatography plates. Elution with 8% methanol in dichloromethane resulted in the development of many minor bands, with a major yellow band streaking from the origin. The major yellow band was extracted with methanol, the resultant solution evaporated to dryness, the residue dissolved in dichloromethane, and the solution filtered and evaporated to dryness. Pumping under high vacuum gave a yellow-brown solid (70 mg, 87% yield). The structure of the product was confirmed by proton NMR spectroscopy.

EXAMPLE 53

Preparation of 3-[2,6-bis(1,1-Dimethylethyl)-(4H-selenopyran-4-ylidene)methyl]-4-hydroxvcyclobut-3-ene-1,2-dione This Example illustrates the preparation, by the reaction D→E shown in FIG. 1, of the squaric acid derivative of Formula II in which $Q^1$ is a 2,6-bis(1,1-dimethylethyl)-4-selenopyrylidene grouping and $R^1$ is a hydrogen atom. 3-[[2,6-bis(1,1-dimethylethyl)-4H-selenopyran-4-ylidene] methyl]-2,4,4-trichlorocyclobut-2-en-1-one (23 g, 52.4 mmole, prepared in Examples 48 and 49 above), trifluoromethane sulfonic acid (80 mL) and water (3 mL) were heated at 105° C. for three hours under nitrogen in a vessel fitted with an outlet connected to a gas-washing bottle containing 10% aqueous sodium hydroxide solution. The resultant dark solution was cooled to room temperature and added slowly to an ice/water mixture with rapid agitation. The resultant red solid was collected by filtration, washed with water and air dried, causing. its color to change to an iridescent green. The crude product so obtained was purified by trituration with cyclohexane for three hours. The pure 3-[[2,6-bis(1,1-dimethylethyl)-4H-selenopyran-4-ylidene] methyl]-4-hydroxycyclobut-3-ene-1,2-dione was collected by filtration, washed with cyclohexane, and dried to afford a red material (18 g, 94% yield). The structure of this compound was confirmed by mass spectroscopy and by $^1$H and $^{13}$C NMR spectroscopy.

EXAMPLE 54

Preparation of 3-[2,6-bis(1,1-Dimethylethyl)-(4H-thiopyran-4-ylidene)-methyl]-4-hydroxycyclobut-3-ene-1,2-dione This Example illustrates the preparation, by a reaction analogous to D→E shown in FIG. 1, of the squaric acid derivative of Formula II in which $Q^1$ is a 2,6-bis(1,1-dimethylethyl)-4-thiopyrylidene grouping and $R^1$ is a hydrogen atom. 3-[2,6-Bis(1,1-dimethylethyl)-(4H-thiopyran-4-ylidene)methyl]-2,4,4-trichlorocyclobut-2-en-1-one (279 mg, 0.59 mmole, prepared in Example 51 above) was added to a solution of trifluoromethane sulfonic acid (1.0 mL) in water (35 mg). The colorless reaction mixture was stirred under nitrogen with heating to 90° C. for 5 hours, after which it was cooled to 20° C. and stirred for 12 hours at that temperature. The reaction mixture was quenched into ice/water (15 mL) dropwise, with efficient agitation. A brown precipitate formed which was initially crystalline, but become gummy after standing for several minutes. This was separated by filtration, washed with dilute aqueous sodium sulfate, and separated into two portions. One portion was dried, to give a red-brown amorphous solid (110 mg). The second portion was partly purified by flash chromatography on silica gel with 10–16–20 % methanol/dichloromethane as eluent to yield a still impure product (55 mg, exhibiting, inter alia, mle 363 in the mass spectrum), which was used directly in Example 70 without further purification.

Part 2.2 : Salt Condensation and Hydrolysis Reactions
Part 2.2.1: Salt/Diacid Chloride Condensations
The following Examples 55 and 56 show the reaction B+F→J shown in FIG. 2, and an analogous reaction.

EXAMPLE 55

Preparation of 4-[[2,6-bis(1,1-Dimethylethyl)seleno-4H-pyran-4-ylidene]methy]-3-chlorocyclobut-3-ene-1,2-dione This Example illustrates the preparation, by the reaction B+F→J shown in FIG. 2, of the squaric acid derivative of Formula VI in which $Q^1$ is a 2,6-bis(1,1-dimethylethyl)-4-selenopyrylidene grouping, $R^1$ is a hydrogen atom and A is a chlorine atom.

Triethylamine (0.67 g, 6.6 mmole) was added dropwise to a solution of 2,6-bis(dimethylethyl)selenopyrylium tetrafluoroborate (1.18 g, 3.3 mmole, prepared in Example I above) and 3,4-dichlorocyclobut-3-ene-1,2-dione (0.50 g, 3.3 mmole, prepared as described in Schmidt, A. H., Synthesis, 1980, 963) in dichloromethane (10 mL) at room temperature over a period of 45 minutes. The reaction mixture was stirred for an additional 7 hours, after which the solvent was removed and diethyl ether (50 mL) was added. The ether solution was filtered and the filtrate was washed with additional ether (50 mL). The ether extracts were reserved, and the solid residue was purified by flash chromatography on silica gel with dichloromethane as the eluent. The chromatographed material was combined with the ether extracts and the resultant solution was concentrated to yield the desired squaric acid derivative as an orange solid (0.62 g, 49% yield). The structure of this compound was confirmed by mass spectroscopy and by $^1$H and $^{13}$C NMR spectroscopy.

EXAMPLE 56

Preparation of 4-[[6-[but-2-oxy]-2-[1,1-Dimethylethyl]benz[b]-4H-pvran-4-ylidene]methyl]-3-chlorocyclobut-3-ene-1,2-dione This Example illustrates the preparation, by a reaction analogous to B+F→J shown in FIG. 2, of the squaric acid derivative of Formula VI in which $Q^1$ is a 6-[but-2-oxy]-2-[1,1-dimethylethyl]benz[b]-4H-pyran4-ylidene grouping, $R^1$ is a hydrogen atom and A is a chlorine atom.

A solution of 6-[but-2-oxy]-2-[1,1-dimethylethyl]-4-methylbenz-pyrylium tetrafluoroborate (10.0 g, 27.8 mmole, prepared in Example 41 above) in acetonitrile (70 mL) was added dropwise over a period of 30 minutes to a solution of 3,4-dichlorocyclobut-3-ene-1,2-dione (4.5 g, 29.8 mmole, prepared as described in Schmidt, A. H., Synthesis, 1980, 963) in a mixture of acetonitrile (10 mL) and N-methylpyrrolidone (NMP, 20 mL), with ice/water cooling. A precipitate quickly formed, and stirring became somewhat difficult. The mixture was then allowed to warm to room temperature and stirring was continued for a further 1 hour, after which the mixture was refrigerated. The product was isolated by filtration, washed with a little cold acetonitrile, and air-dried to give a dark orange powder (6.71 g, 62% yield) which was pure enough for direct use in Example 60 below. The structure of this compound was confirmed by mass spectroscopy and by $^1$H and $^{13}$C NMR spectroscopy.
Part 2.2.2: Salt/Monoester Monoacid Chloride Condensation The following Example illustrates the preparation, by the reaction B+G→K shown in FIG. 2, of the squaric acid derivative of Formula IV in which $Q^1$ is a 2,6-bis(1,1-dimethylethyl)-4-selenopyrylidene grouping, $R^1$ is a hydrogen atom and A' is a methoxy group.

EXAMPLE 57

Preparation of 4-[[2.6-bis(1,1-Dimethylethyl)seleno-4H-pyran-4-ylidene]methyl]-3-methoxycyclobut-3-ene-1,2-dione A solution of triethylamine (76 mg, 0.75 mmole) in dichloromethane (2 mL) was added dropwise over 30 minutes to a solution of 3-chloro-4-methoxy-cyclobut-3-ene-1,2-dione (100 mg, 0.68 mmole, prepared in Example 46 above) and 2,6-bis(1,1-dimethylethyl)-4-methylselenopyrylium tetrafluoroborate (244 mg, 0.68 mmole, prepared in Example 1 above) in dichloromethane (5 mL) at room temperature, and the resultant mixture was allowed to stand at room temperature for 1 hour. The solvent was then removed and the residue was extracted with hexanes. The extracts were filtered and concentrated under reduced pressure, and the resultant red oil was dissolved in methanol and allowed to stand at 5° C. for two days. The solvent was then removed and the crude product was purified by preparative thin layer chromatography on silica gel with 4% methanol/ dichloromethane as eluent to give the ester as a red oil (50 mg, 19% yield). The structure of this compound was confirmed by mass spectroscopy and by $^1$H and $^{13}$C NMR spectroscopy.
Part 2.2.3 Salt/Diester Condensation The following Example illustrates the preparation, by a reaction analogous to B+H→K shown in FIG. 2, of the squaric acid derivative of Formula VI in which $Q^1$ is a 7-diethylamino-2-(1,1-dimethylethyl)benz[b]-4H-pyran--4-ylidene grouping, $R^1$ is a hydrogen atom and A is an n-butoxy group. The diester (the analogue of H) used is the di-n-butyl ester of squaric acid.

EXAMPLE 58

Preparation of 4-[[7-Diethylamino-2-(1,1-dimethylethyl)benz[b]-4H-pyran-4-ylidene]methyl]-3-butoxycyclobut-3-ene-1,2-dione A solution of 7-diethylamino-2-(1,1-dimethylethyl)-4-methylbenz-pyrylium tetrafluoroborate (3.57 g, 10 mmole, prepared as described in copending application Ser. No. 07/795,038, filed Nov. 20, 1991) in dichloromethane (20 mL) was added dropwise over two hours to a solution of di-n-butyl squarate (2.5 g, 11 mmole, available from Aldrich Chemical Company, Milwaukee, Wis.) and triethylamine (2.02 g, 20 mmole) in dichloromethane (30 mL) at room temperature. After the addition had been completed, the reaction mixture was heated under reflux for three hours. The solvent was then removed and diethyl ether (50 mL) was added. The ether solution was filtered and the solid residue was washed with more ether (50 mL). The combined ether extracts were concentrated, and the crude product thus obtained was purified by flash chromatography on silica gel with 30% ether/hexanes as eluent to give 4-[[7-diethylamino-2-(1,1-dimethyl-ethyl)benz[b]-4H-pyran-4-ylidene]methyl]-3-butoxy-cyclobut-3-ene-1,2-dione as a red solid (1.35 g, 29% yield) which melted at 145–146° C. The structure of this compound was confirmed by mass spectroscopy and by $^1$H and $^{13}$C NMR spectroscopy.

(The filtrate from the ether extraction was collected, dissolved in dichloromethane, washed sequentially with 1M hydrochloric acid, a saturated solution of sodium hydrogen carbonate and brine, and dried over magnesium sulfate. Removal of solvent yielded 3,4-bis[[7-diethylamino-2-(1,1-dimethylethyl)benz[b]-4H-pyran-4-ylidene]methyl]cyclobut-3-ene-1,2-dione as a green solid (1.14 g, 37% yield) which did not melt below 300° C. The structure of this compound was confirmed by mass spectroscopy and by $^1$H and $^{13}$C NMR spectroscopy.)

Part 2.2.4 : Acid Chloride Hydrolysis

The following Examples 59 and 60 illustrate the hydrolysis reaction J→E shown in FIG. 1, and an analogous reaction.

EXAMPLE 59

Preparation of 4-[[2,6-bis(1,1-Dimethylethyl)seleno-4H-pyran-4-ylidene]methyl]-3-hydroxy-cyclobut-3-ene-1,2-dione This Example illustrates the preparation, by the reaction J→E shown in FIG. 1, of the squaric acid derivative of Formula II in which $Q^1$ is a 2,6-bis(1,1-dimethylethyl)-4-selenopyrylidene grouping and $R^1$ is a hydrogen atom.

A solution of 4-[[2,6-bis(1,1-dimethylethyl)selenopyran-4-ylidene]-methyl]-3-chloro-cyclobut-3-ene-1,2-dione (212 mg, 0.55 mmole, prepared in Example 55 above) in tetrahydrofuran (10 mL) containing water (2 mL) was heated at reflux for 7 hours. After cooling to room temperature, the mixture was concentrated under reduced pressure. The crude product so obtained was triturated with hexanes, collected by vacuum filtration and washed with more hexanes to give the acid (140 mg, 69% yield) as a red powder. The structure of this compound was confirmed by mass spectroscopy and by $^1$H and $^{13}$C NMR spectroscopy. This material was identical, by $^1$H NMR spectroscopy, to material prepared in Example 48 above.

EXAMPLE 60

Preparation of 4-[[6-[but-2-oxy]-2-[1,1-dimethylethyl]benz[b]-4H-pvran-4-ylidene]methyl]-3-hydroxvcyclobut-3-ene-1,2-dione This Example illustrates the preparation, by a reaction analogous to J→E shown in FIG. 1, of the squaric acid derivative of Formula II in which $Q^1$ is a 6-[but-2-oxy]-2-[1,1-dimethylethyl]benz[b]-4H-pyran-4-ylidene grouping and $R^1$ is a hydrogen atom.

Water (5 mL) was added to a solution of 4-[[6-[but-2-oxy]-2-[1,1-dimethylethyl]benz[b]-4H-pyran-4-yldene]methyl]-3-chlorocyclobut-3-ene-1,2-dione (2.55 g, 6.6 mmole, prepared in Example 56 above) in THF (20 mL) and the solution was heated to reflux for 27 hours. The solvents were then removed and the residue was triturated with hexanes. The solid material remaining was collected and dried, affording the acid as a brick-red powder (2.07 g, 85% yield). The structure of this compound was confirmed by mass spectroscopy and by $^1$H and $^{13}$C NMR spectroscopy.

Part 2.2.5 : Ester Hydrolysis

The following Examples 61 and 62 illustrate the hydrolysis reaction K→E shown in FIG. 1, and an analogous reaction.

EXAMPLE 61

Preparation of 4-[[2,6-bis(1,1-Dimethylethyl)seleno-4H-pyran-4-ylidene]methyl]-3--hydroxycyclobut-3-ene-1,2-dione This Example illustrates the preparation, by the reaction K→E shown in FIG. 1, of the squaric acid derivative of Formula II in which $Q^1$ is a 2,6-bis(1,1-dimethylethyl)-4-selenopyrylidene grouping and $R^1$ is a hydrogen atom.

A solution of 4-[[2,6-bis(1,1-dimethylethyl)seleno-4H-pyran-4-ylidene]-methyl]-3-methoxy-cyclobut-3-ene-1,2-dione (25 mg, 0.066 mmole, prepared in Example 57 above) in tetrahydrofuran (4 mL) containing 1M hydrochloric acid (0.2 mL) was heated at reflux for 6 hours, then cooled to room temperature and stored for 16 hours. The solution was then concentrated under reduced pressure (water being removed by azeotropic distillation with toluene (3×10 mL)) to afford the acid as a purplish solid (21.6 mg, 90% yield). The structure of this compound, which was found to be slightly impure by $^1$H NMR, was determined by $^1$H and $^{13}$C NMR spectroscopy to be the same as that of the material prepared in Example 59 above.

EXAMPLE 62

Preparation of 4-[[7-Diethylamino-2-(1,1-dimethylethyl)benz[b]-4H-pyran-4-ylidene]methyl]-3-hydroxycyclobut-3-ene-1,2-dione This Example illustrates the preparation, by a reaction analogous to K→E shown in FIG. 1, of the squaric acid derivative of Formula II in which $Q^1$ is a 7-diethylamino-2-(1,1-dimethylethyl)benz[b]-4H-pyran-4-ylidene grouping and $R^1$ is a hydrogen atom.

A solution of 4-[[7-diethylamino-2-(1,1-dimethylethyl) benz[b]-4H-pyran-4-ylidene]methyl]-3-butoxy-cyclobut-3-ene-1,2-dione (200 mg, 0.47 mmole, prepared in Example 58 above) in tetrahydrofuran (5 mL) containing 1M hydrochloric acid (0.5 mL) was heated at reflux for 6 hours, then cooled to room temperature and allowed to stand for 15 hours. The mixture was then concentrated under reduced pressure, excess water being removed by azeotropic distillation with toluene (2×10 mL). The crude product so obtained was triturated with ether, collected by vacuum filtration and washed with more ether to give the acid (148 mg, 86% yield) as a yellow powder, which decomposed at 172–173° C. The structure of this compound was confirmed by mass spectroscopy and by $^1$H and $^{13}$C NMR spectroscopy.

Part 2.3 : Chromone Condensation Reaction

The following Example illustrates the reaction R+Q→S shown in FIG. 4.

EXAMPLE 63

Preparation of 4-[[[2-[1,1-Dimethylethyl]benz[b]-4H]-thiopyran-4-ylidene]methyl]-3-butoxycyclobut-3-ene-1,2-dione Trifluoromethane sulfonic anhydride (258 mg, 0.92 mmole) was added to a solution of 2-[1,1-dimethylethyl]benz[b]-4H-thiopyran-4-one (177.7 mg, 0.92 mmole, prepared in Example 44 above) in dichloromethane (0.4 mL). A yellow color and precipitate immediately appeared. A solution of 3-butoxy-4-methylcyclo-but-3-ene-1,2-dione (154 mg, 0.92 mmole, prepared as described in L. Liebeskind et al., J. Org. Chem., 53, 2482 (1988)) in dichloromethane (1 mL) was next added, followed by a solution of triethylamine (92.5 mg, 0.92 mmole) in dichloromethane (0.5 mL). A red-brown suspension formed. A further quantity of triethylamine (92.5 mg, 0.92 mmole) was then added, and the reaction mixture was stirred at 20° C. for 1.5 hours. The reaction mixture was then quenched by addition of 1M hydrochloric acid (3 mL), the layers were separated, and the organic layer was washed with water (2.5 mL), separated, and stored for 17 hours. The resultant solution was then purified by preparative thin-layer chromatography on silica gel with 0, 0.2, 0.5, 1, 1.5, 2, 3, 5 and 7% methanol/dichloromethane solutions as successive eluents. The desired derivative was isolated as a red-orange solid (57.6 mg, 17% yield). The structure of this compound was confirmed by mass spectroscopy and by $^1$H NMR spectroscopy.

PART 3: PREPARATION OF DYES

Part 3.1: Salt Dye-Forming Reactions

The following Examples 64–70 illustrate the reaction E+L→A shown in FIG. 1, and analogous reactions.

EXAMPLE 64

Preparation of 4-[[[3-2,6-bis(1,1-Dimethylethyl)-(4H-pyran-4-ylidene)-methyl]-2-hydroxy-4-oxo-2-cyclobuten-1-ylidene]methyl]-2,6-bis(1,1-dimethylethyl)-thiopyrylium Hydroxide Inner Salt Dye This Example illustrates the preparation, by a reaction analogous to E+L→A shown in the drawing, of the squarate dye of Formula I in which $Q^1$ is a 2,6-bis(1,1-dimethylethyl)-4-pyrylidene grouping, $Q^2$ is a 2,6-bis(1,1-dimethyl-ethyl)-4-thiopyrylium grouping, and $R^1$ and $R^2$ are each a hydrogen atom. 3-[2,6-Bis(1,1-dimethylethyl)-(4H-pyran-4-ylidene)methyl]-4-hydroxy-cyclobut-3-ene-1,2-dione (60 mg, 0.2 mmole, prepared in Example 52 above) and 2,6-bis(1,1-dimethylethyl)4-methylthiopyrylium tetrafluoroborate (62 mg, 0.2 mrnole, prepared as described in U.S. Pat. No. 4,343,948) were mixed with n-butanol (2 mL) and distilled quinoline (23 EL). The resultant mixture was heated at 100° C. for 4 hours, then evaporated to dryness. The residue was partitioned between dichloromethane and water, and the dichloromethane layer separated, washed with water, dried over sodium sulfate and evaporated to dryness. The residue was placed on two preparative silica chromatography plates and eluted with a 1:1 v/v ethyl acetate/dichloromethane mixture. The resulting greenish band was excised, ground in a mortar and extracted with 5% methanol in ethyl acetate. The resultant solution was evaporated to dryness and the residue triturated with dichloromethane. The solution was filtered and evaporated to dryness under high vacuum to give the dye as a greenish metallic crystalline solid (32 mg, 32% yield based on the squarate starting material). The structure of the dye was confirmed by FAB mass spectroscopy and by proton NMR spectroscopy. The dye had a strong infra-red absorption at 768 nm in dichloromethane solution, $\epsilon$=285,000.

EXAMPLE 65

Preparation of 4-[[[3-2,6-bis(1,1-Dimethylethyl)-(4H-selenopyran-4-ylidene)methyl]-2-hydroxy-4-oxo-2-cyclobuten-1-ylidene]methyl]-2,6-bis-(1,1-dimethylethyl)pyrylium Hydroxide Inner Salt Dye This Example illustrates the preparation, by the reaction E+L→A shown in FIG. 1, of the squarate dye of Formula I in which $Q^1$ is a 2,6-bis(1,1-dimethylethyl)-4-pyrylidene grouping, $Q^2$ is a 2,6-bis(1,1-dimethylethyl)-4-selenopyrylium grouping, and $R^1$ and $R^2$ are each a hydrogen atom.

A 100 mL three-necked round-bottom flask was equipped with a magnetic stirrer, a thermometer, a reflux condenser with a dry nitrogen gas inlet tube and an outlet attached to a succession of scrubbers containing 10% aqueous sodium hydroxide and 10% aqueous lead acetate. Into this flask were placed crude 3-[2,6-bis(1,1-dimethylethyl)-(4H-selenopyran-4-ylidene)methyl]-4-hydroxycyclobut-3-ene-1,2-dione (2.13 g, 5.02 mmole, prepared in Example 53 above), 2,6-bis(1,1-dimethylethyl)-4-methylpyrylium trifluoromethane sulfonate (1.79 g, 5.02 mmole, prepared as described in Organic Syntheses, 60, 34-39), redistilled quinoline (0.69 mL, 5.8 mmole) and n-butanol (40 mL). Stirring was begun and the reaction mixture was heated at 100° C. under nitrogen for 1.5 hours; after this time, thin layer chromatography showed the complete disappearance of the dione starting material. The solvent and the quinoline were completely removed by distillation in vacuo, the blue-black residue was suspended in water (150 mL) and the suspension was extracted with two 150 mL aliquots of dichloromethane. The separated dichloromethane extracts were combined, washed with three 150 mL aliquots of water and dried over sodium sulfate. The drying agent was removed by filtration and the filtrate evaporated to dryness in a rotary evaporator on a water bath kept at approximately 40° C. The resultant blue-black solid was dried in vacuo at approximately 30° C. to give the crude product (3.5 g, approximately 100% yield).

This crude product was purified by medium pressure reversed phase chromatography using a column prepared by slurrying Whatman Partisil 40 ODS 3 bulk medium (sold by Whatman International Ltd, Maidstone, Kent, England) in 10% methanol in water. In use, this column was eluted continuously with 10% water in methanol (1.5 L) under a medium pressure of nitrogen.

The 3.5 g of crude dye was dissolved in 10% water in methanol (650 mL) and filtered; a very small quantity of dark particles was collected on the filter paper. The dye solution was chromatographed on the pre-eluted column under a medium pressure of nitrogen, and 125 mL fractions of eluent were collected. Each fraction was tested by thin layer chromatography using silica gel and a 1:1 v/v ethyl acetate/ dichloromethane mixture as eluent. The fractions containing the desired product were combined and reduced to approximately 100 mL in volume using a rotary evaporator on a water bath kept at approximately 40° C. A solution of sodium chloride (5 g) in water (10 mL) was added to the concentrate, and the resultant mixture extracts with three 120 mL aliquots of dichloromethane. The dichloromethane extracts were combined and dried over sodium sulfate. The drying agent was then removed by filtration and washed with dichloromethane until the washings were colorless. The filtrate and washings were combined and reduced to approximately 3 mL in volume using a rotary evaporator on a water bath kept at approximately 40° C. The resultant residue crystallized after 1 hour at room temperature under a slow stream of nitrogen to olive-green crystals, which were dried in vacuo at approximately 30° C. over calcium sulfate overnight, to give the desired dye (0.8 g). An additional 0.31 g of the same product was isolated from earlier fractions by the same procedure used for the main fractions, for a total yield of 1 .1 g, 40% based upon the dione starting material. The structure of the dye was confirmed by FAB mass spectroscopy and by proton NMR spectroscopy. The dye had a strong infra-red absorption at 779 nm in dichloromethane solution, $\epsilon=265,000$.

EXAMPLE 66

Preparation of 4-[[[3-2,6-bis(1,1-Dimethylethyl)-(4H-selenopyran-4-ylidene)methyl]-2-hydroxy-4-oxo-2-cyclobuten-1-ylidene]methyl]-2,6-bis-(1,1-dimethylethyl)pyrylium hydroxide inner salt dye This Example illustrates an improved preparation of the same squarate dye of Formula I as in Example 65 above.

A solution of 3-[[2,6-bis(1,1-dimethylethyl)-4H-selenopyran-4-ylidenel-methyl]-4-hydroxycyclobut-3-ene-1,2-dione (6.9 g, 18.9 mmole, prepared in Example 53 above), 2,6-bis(1,1-dimethylethyl)-4-methylpyrylium trifluoromethane sulfonate (7.1 g, 19.9 mmole, prepared as described in Organic Syntheses, 60, 34–39) and quinoline (6.7 g, 20.9 mmole) in n-butanol (100 mL) was heated at 105° C. for 90 minutes, then allowed to cool to room temperature. The resultant green solution was poured into an ice-cold 6:4 methanol/water mixture (1 L) with rapid stirring. The resultant solid was collected by filtration and air-dried, giving the crude dye (7.3 g). Purification was accomplished by trituration with boiling hexanes for 20 minutes. The product was filtered while hot, washed with hexanes and air-dried, yielding the dye as golden crystals (6.5 g, 62% yield). High Pressure Liquid Chromatographic analysis indicated this material to be 99% pure by weight. This material was spectroscopically identical to material prepared in Example 65 above.

EXAMPLE 67

Preparation of 4-[3-[[7-Diethylamino-2-(1,1-dimethylethyl)benz[b]-4H-pyran-4-ylidene]methyl]-2-hydroxU-4-oxo-2-cyclobuten-1-ylidene]methyl]-7-diethyl-amino-2-phenylbenzpyrylium hydroxide inner salt dye This Example illustrates the preparation, by a reaction analogous to E+L→A shown in FIG. 1, of the dye of Formula I in which $Q^1$ is a 7-diethyl-amino-2-[1,1-dimethylethyl]benz[b]-4H-pyran-4-ylidene grouping, $Q^2$ is a 7-diethyl-amino-2-phenylbenzpyrylium grouping, and $R^1$ and $R^2$ are each a hydrogen atom.

A solution of 4-[[7-diethylamino-2-[1,1-dimethylethyl] benz[b]-4H-pyran-4-ylidene]methyl]-3-hydroxycyclobut-3-ene-1,2-dione (14.6 mg, 0.04 mmole, prepared in Example 62 above), 7-diethylamino-4-methyl-2-phenylbenz[b]-pyrylium tetrafluoroborate (15.2 mg, 0.04 mmole, prepared in Example 23 above) and quinoline (10.2 mg, 0.08 mmole) in n-butanol (1 mL) was heated to reflux for 30 minutes. The solvent was then removed under reduced pressure, and the crude material was purified by. preparative thin-layer chromatography on silica gel with successive elutions with 2% and 3% methanol/dichloromethane. The dye (3.2 mg, 12% yield) was obtained as a coppery powder. The dye exhibited a near infra-red absorption at 836 nm in dichloromethane solution, $\epsilon=198,000$. The structure of this compound was confirmed by mass spectroscopy and by $^1$H and $^{13}$C NM spectroscopy.

EXAMPLE 68

Preparation of 4-[[3-[2,6-bis[1,1-Dimethylethyl]-[4H-selenopyran-4-ylidene]methyl]-2-hydroxy-4-oxo-2-cyclobuten-1-ylidene]methyl]-2-[2-trifluoromethylphenyl]benz[b]pyrylium hydroxide inner salt dye This Example illustrates the preparation, by a reaction analogous to E+L→A shown in FIG. 1, of the squarate dye of Formula I in which $Q^1$ is a 2,6-bis[1,1-dimethylethyl]-4-selenopyrylidene grouping, $Q^2$ is a2-[2-trifluoromethylphenyl]benz[b]pyrylium grouping, and $R^1$ and $R^2$ are each a hydrogen atom.

A solution of 3-[2,6-bis[1,1-dimethylethyl]-[4H-selenopyran-4ylidene]-methyl]-4-hydroxycyclobut-3-ene-1, 2-dione (200 mg, 0.29 mmole, prepared in Example 53), 2-[2-trifluoromethylphenyl]benz[b] pyrylliumtetrafluoroborate (100 mg, 0.27 mmole, prepared in Example 28 above) and quinoline (37 mg, 0.29 mmole) in n-butanol (5 mL) was heated to reflux for 2 hours, then cooled and allowed to stand at room temperature for 17 hours. The solvent was then removed under reduced pressure, and the crude material was triturated with ether. The solid residue remaining after trituration was purified by preparative thin-layer chromatography on silica gel with 2% methanol/dichloromethane as eluent, to give the dye (36 mg, 21% yield) as a black powder. The dye exhibited a near infra-red absorption at 812 nm, $\epsilon=140,000$. The structure of this compound was confirmed by mass spectroscopy and by $^1$H NMR spectroscopy.

EXAMPLE 69

Preparation of 4-[[3-[[6-[but-2-oxy]-2-[1,1-Dimethylethyl]benz[b]-4H-pyran-4-ylidene]methyl]-2-hydroxy-4-oxo-2-cyclobuten-1-ylidene]methyl]-6-[2-ethylbut-1-oxy]-2-phenylbenzpyrylium hydroxide inner salt dye This Example illustrates the preparation, by a reaction analogous to E+L→A shown in FIG. 1, of the dye of Formula I in which $Q^1$ is a 6-[but-2-oxy]-2-[1,1-dimethylethyl]benz[b]-4H-pyran-4-ylidene grouping, $Q^2$ is a 6-[2-ethyl-but-1-oxy]-2-phenylbenzpyrylium grouping, and $R^1$ and $R^2$ are each a hydrogen atom.

Quinoline (0.025 mL, 0.22 mmole) was added to a solution of 4-[[6-[but-2-oxy]-2-[1,1 -dimethylethyl]benz[b]-

4H-pyran-4-ylidene]methyl]-3-hydroxycyclobut-3-ene-1,2-dione (50 mg, 0.14 mmole, prepared in Example 60 above) and 6-[2-ethylbut-1-oxy]-4-methyl-2-phenylbenzpyrylium tetrafluoroborate (57 mg, 0.14 mmole, prepared in Example 38 above) in n-butanol (2 mL) at room temperature, and the reaction flask (which was fitted with a reflux condenser) was placed in an oil bath, which had been pre-heated to 150° C. The reaction mixture was heated at reflux for 20 minutes, then cooled and diluted with acetone (5 mL). The solvent was removed with a stream of nitrogen, and acetone (3 mL) was added to the residue. The remaining solid material was removed by filtration, washed with acetone and air-dried to afford the dye (34 mg, 36% yield) as greenish-copper crystals. The dye had an absorbance at 817 nm in dichloromethane solution. The structure of this compound was confirmed by mass spectroscopy and by $^1$H and $^{13}$C NMR spectroscopy.

EXAMPLE 70

Preparation of 4-[[3-[2,6-bis[1,1-dimethylethyl]-[4H-thiopyran-4-ylidene]methyl]-2-hydroxy-4-oxo-2-cyclobuten-1-ylidene]methyl]-2,6-bis[2,4-dimethylphenyl]pyrylium hydroxide inner salt dye This Example illustrates the preparation, by a reaction analogous to E+L→A shown in FIG. 1, of the squarate dye of Formula I in which $Q^1$ is a 2,6-bis[1,1-dimethylethyl]-4-thiopyrylidene grouping, $Q^2$ is a 2,6-bis[2,4-dimethylphenyl]pyrylium grouping, and $R^1$ and $R^2$ are each a hydrogen atom.

A mixture of 3-[2,6-bis[1,1-dimethylethyl]-[4H-thiopyran-4-ylidene]-methyl]-4-hydroxycyclobut-3-ene-1,2-dione (37 mg, 0.116 mmole, prepared in Example 54 above), 2,6-bis[2,4-dimethylphenyl]-4-methylpyrylium triflate (45 mg, 0.099 mmole, prepared from 2,4-dimethylbenzoyl chloride and t-butanol by a method analogous to that described in Anderson and Stand, J. Org. Chem., 41, 3034 (1976)) and quinoline (13 mg, 0.101 mmole) in n-butanol (2.0 mL) was stirred at reflux for 35 minutes. The reaction mixture was then concentrated under reduced pressure at below 45° C., and diluted with dichloromethane (3 mL). The resulting solution was washed with hydrochloric acid (4 mL of a 4M solution). The organic layer was separated, dried and concentrated, and the residue was purified by flash chromatography on silica gel with 1.5% methanol/dichloromethane as eluent. The dye was further purified by trituration with methyl t-butyl ether to afford metallic, brick-red prisms (37.4 mg). The mother liquors were also purified by preparative thin-layer chromatography on silica gel with 2.2% methanol/dichloromethane as eluent to give a further 5.6 mg of dye. The combined yield was 43.7 mg, 73%. The dye exhibited a strong absorption in the near infra-red at 714 nm in dichloromethane solution, $\epsilon=251,000$. The structure of this compound was confirmed by mass spectroscopy and by $^1$H NMR spectroscopy.

Part 3.2: Aromatic Dye-Forming Reaction

The following Example illustrates the dye forming reaction shown in FIG. 8.

EXAMPLE 71

Preparation of 4-[[3-[4-Diethylaminophenyl]-2-hydroxy-4-oxo-2-cyclobuten-1-ylidene]methyl]-6-[but-2-oxy]-2-[1,1-dimethylethyl]benzpvrylium hydroxide inner salt dye A solution of 4-[[6-[but-2-oxy]-2-[1,1-dimethylethyl]benz[b]-4H-pyran-4-ylidene]methyl]-3-hydroxycyclobut-3-ene-1,2-dione (50 mg, 0.14 mmole, prepared in Example 60 above), diethylaminobenzene (0.025 mL, 0.16 mmole) and triethyl orthoformate (0.1 mL, 0.6 mmole) in 3-pentanol (2 mL) was heated at reflux for 17 hours. The solvent was then removed under reduced pressure, and the residue was purified by flash chromatography on silica gel with gradient elution from dichloromethane to 2% methanol/dichloromethane. The dye was isolated as greenish crystals (6 mg, 8% yield). A dichloromethane solution of the dye absorbed at 744 nm. The structure of this compound was confirmed by mass spectroscopy and by $^1$H and $^{13}$C NMR spectroscopy.

What is claimed is:
1. A squarylium compound of the formula:

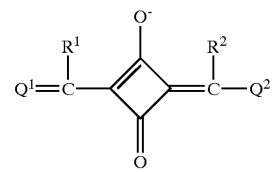

wherein $Q^1$ and $Q^2$ are each independently a pyrylium, thiopyrylium, selenopyrylium, benzpyrylium, benzthiopyrylium or benzselenopyrylium nucleus, and $R^1$ and $R^2$ are each independently a hydrogen atom or an aliphatic or cycloaliphatic group, the $Q^1CR^1$ grouping being different from the $Q^2CR^2$ grouping.

2. A squarylium compound according to claim 1 which is essentially free from squarylium compounds of the formulae:

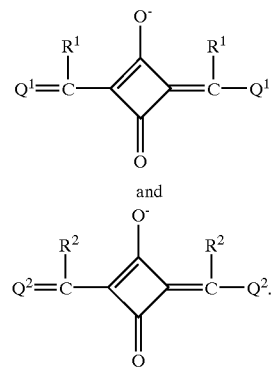

3. A squarylium compound according to claim 2 wherein each of $Q^1$ and $Q^2$ is a 4-pyrylium, 4-thiopyrylium, 4-selenopyrylium, 4-benzpyrylium, 4-benzthiopyrylium or 4-benzselenopyrylium nucleus.

4. A squarylium compound according to claim 3 wherein at least one of $Q^1$ and $Q^2$ is a 2,6-dialkylpyrylium, -thiopyrylium or -selenopyrylium nucleus, in which each of the alkyl groups contains not more than about 8 carbon atoms.

5. A squarylium compound according to claim 4 wherein at least one of $Q^1$ and $Q^2$ is a 2,6-di-tertiary butylpyrylium, -thiopyrylium or -selenopyrylium nucleus.

6. A squarylium compound according to claim 3 wherein one of $Q^1$ and $Q^2$ is a 2-phenyl benzpyrylium, benzthiopyrylium or benzselenopyrylium nucleus and the other is (a) a 2-substituted benzpyrylium, benzthiopyrylium or benzselenopyrylium nucleus, in which the 2-substituent is an alkyl, alkenyl, alkynyl or alkicyclic group, or (b) a 2,6-dialkyl butylpyrylium, -thiopyrylium or -selenopyrylium nucleus.

7. A squarylium compound according to claim 6 wherein the 2-phenyl group has an ortho alkoxy or cycloalkoxy substituent.

8. A squarylium compound according to claim 3 wherein one of $Q^1$ and $Q^2$ is a benzpyrylium, benzthiopyrylium or benzselenopyrylium nucleus bearing at its 7-position an —N[(CH$_2$)$_3$—]$_2$ grouping in which the ends of the trimethylene groups remote from the nitrogen atom are joined to the 6- and 8-positions of the nucleus, so that the —N[—(CH$_2$)$_3$—]$_2$ grouping and the phenyl ring of the nucleus together form a julolidine ring system, and the other is (a) a 2-substituted benzpyrylium, benzthiopyrylium or benzselenopyrylium nucleus, in which the 2-substituent is an alkyl, alkenyl, alkynyl or alicyclic group, or (b) a 2,6-dialkyl-pyrylium, -thiopyrylium or -selenopyrylium nucleus.

9. A squarylium compound according to claim 3 wherein at least one of $Q^1$ and $Q^2$ is a benzpyrylium, benzthiopyrylium or benzselenopyrylium nucleus bearing at its 6-position an alkoxy or cycloalkoxy group.

10. A squarylium compound according to claim 1 in which:
   (a) $Q^1$ is a 2,6-bis(1,1-dimethylethyl)-4-pyrylidene grouping, $Q^2$ is a 2,6-bis(1,1-dimethylethyl)-4-thiopyrylium grouping, and $R^1$ and $R^2$ are each a hydrogen atom, namely [4-[[3-2,6-bis(1,1-dimethylethyl)-(4H-pyran-4-ylidene)-methyl]-2-hydroxy-4-oxo-2-cyclobuten-1-ylidene]methyl]-2,6-bis(1,1-dimethyl-ethyl)thiopyrylium hydroxide inner salt;
   (b) $Q^1$ is a 2,6-bis(1,1-dimethylethyl)-4-pyrylidene grouping, $Q^2$ is a 2,6-bis(1,1-dimethylethyl)-4-selenopyrylium grouping, and $R^1$ and $R^2$ are each a hydrogen atom, namely [4-[[3-2,6-bis(1,1-dimethylethyl)-(4H-pyran-4-ylidene)-methyl]-2-hydroxy-4-oxo-2-cyclobuten-1-ylidene]methyll-2,6-bis(1,1-dimethylethyl)-selenopyrylium hydroxide inner salt;
   (c) $Q^1$ is a 7-diethylamino-2-(1,1-dimethylethyl)benz[b]-4H-pyran-4-ylidene grouping, $Q^2$ is a 7-diethylamino-2-phenylbenzpyrylium grouping, and $R^1$ and $R^2$ are each a hydrogen atom, namely 4-[3-[[7-diethylamino-2-(1,1-dimethylethyl)benz[b]-4H-pyran-4-ylidene] methyl]-2-hydroxy-4-oxo-2-cyclobuten-1-ylidene] methyl]-7-diethylamino-2-phenylbenzpyrylium hydroxide inner salt dye;
   (d) $Q^1$ is a 2,6-bis[1,1-dimethylethyl]-4-selenopyrylidene grouping, $Q^2$ is a 2-[2-trifluoromethylphenyl]benz[b] pyrylium grouping, and $R^1$ and $R^2$ are each a hydrogen atom, namely 4-[[3-[2,6-bis[1,1-dimethylethyl]-[4H-selenopyran-4-ylidene]methyl]-2-hydroxy-4-oxo-2-cyclobuten-1 -ylidene]methyl]-2-[2-trifluoromethylphenyl]benz[b]pyrylium hydroxide inner salt dye;
   (e) $Q^1$ is a 6-[but-2-oxy]-2-[1,1-dimethylethyl]benz[b]-4H-pyran-4-ylidene grouping, $Q^2$ is a 6-[2-ethylbut-1-oxy]-2-phenylbenzpyrylium grouping, and $R^1$ and $R^2$ are each a hydrogen atom, namely 4-[[3-[[6-[but-2-oxy]-2-[1,1-dimethylethyl]benz[b]-4H-pyran-4-ylidene]methyl]-2-hydroxy-4-oxo-2-cyclobuten-1-ylidene]methyl]6-[2-ethylbut-1-oxy]-2-phenylbenzpyrylium hydroxide inner salt dye; and
   (f) $Q^1$ is a 2,6-bis[1,1-dimethylethyl]-4-thiopyrylidene grouping, $Q^2$ is a 2,6-bis[2,4-dimethylphenyl]pyrylium grouping, and $R^1$ and $R^2$ are each a hydrogen atom, namely 4-[[3-[2,6-bis[1,1-dimethylethyl]-[4H-thiopyran-4-ylidene]-methyl]-2-hydroxy-4-oxo-2-cyclobuten-1-ylidene]methyl]-2,6-bis[2,4-dimethylphenyl]-pyrylium hydroxide inner salt dye.

* * * * *